United States Patent
Bontus et al.

(10) Patent No.: US 7,822,171 B2
(45) Date of Patent: Oct. 26, 2010

(54) CONE BEAM COMPUTED TOMOGRAPHY WITH MULTIPLE PARTIAL SCANNING TRAJECTORIES

(75) Inventors: Claas Bontus, Hamburg (DE); Thomas Koehler, Norderstedt (DE); Peter Koken, Hamburg (DE); Andy Ziegler, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 159 days.

(21) Appl. No.: 12/296,945

(22) PCT Filed: Apr. 19, 2006

(86) PCT No.: PCT/IB2006/050497

§ 371 (c)(1),
(2), (4) Date: Oct. 13, 2008

(87) PCT Pub. No.: WO2007/119124

PCT Pub. Date: Oct. 25, 2007

(65) Prior Publication Data

US 2009/0262885 A1  Oct. 22, 2009

(51) Int. Cl.
 *A61B 6/00* (2006.01)
(52) U.S. Cl. ............... 378/11; 378/4; 378/15
(58) Field of Classification Search ........ 378/4, 378/11, 15
See application file for complete search history.

(56) References Cited

U.S. PATENT DOCUMENTS

| | | | |
|---|---|---|---|
| 5,278,884 A * | 1/1994 | Eberhard et al. | 378/4 |
| 5,463,666 A * | 10/1995 | Eberhard et al. | 378/4 |
| 5,887,047 A * | 3/1999 | Bailey et al. | 378/4 |
| 5,926,521 A | 7/1999 | Tam | |
| 5,999,587 A * | 12/1999 | Ning et al. | 378/4 |
| 6,014,419 A | 1/2000 | Hu | |
| 6,154,515 A * | 11/2000 | Lin et al. | 378/4 |
| 6,430,253 B1 * | 8/2002 | Oikawa | 378/15 |

(Continued)

FOREIGN PATENT DOCUMENTS

WO  2005023114 A2  3/2005

OTHER PUBLICATIONS

Bontus, C., et al.; A quasiexact reconstruction algorithm for helical CT using a 3-Pi acquisition; 2003; Med. Phys.; 30(9)2493-2502.

(Continued)

*Primary Examiner*—Allen C. Ho
*Assistant Examiner*—Alexander H Taningco

(57) ABSTRACT

A computer tomography apparatus (100) for examination of an object of interest (107) comprising an electromagnetic radiation source (104) adapted to emit electromagnetic radiation to an object of interest (107), a detecting device (108) adapted to detect electromagnetic radiation generated by the electromagnetic radiation source (104) and passed through the object of interest (107), and a motion generation device (101, 119) adapted to move the electromagnetic radiation source (104) and the detecting device (108) with respect to the object of interest (107) along a first trajectory and along a second trajectory which differs from the first trajectory, wherein the second trajectory is selected in such a manner that electromagnetic radiation detected during performing the second trajectory provides data which complete mathematically incomplete data detected during performing the first trajectory to thereby allow a reconstruction of structural information concerning the object of interest (107).

34 Claims, 11 Drawing Sheets

U.S. PATENT DOCUMENTS

| | | |
|---|---|---|
| 6,560,308 B1 * | 5/2003 | Zmora .......................... 378/4 |
| 6,763,081 B2 * | 7/2004 | Tam .............................. 378/4 |
| 2002/0037068 A1 * | 3/2002 | Oikawa ....................... 378/15 |
| 2002/0131544 A1 | 9/2002 | Aradate et al. |
| 2004/0086074 A1 * | 5/2004 | Taguchi ........................ 378/4 |
| 2005/0147202 A1 * | 7/2005 | Grass et al. ................. 378/19 |
| 2005/0152494 A1 * | 7/2005 | Katsevich ................... 378/62 |
| 2006/0034417 A1 | 2/2006 | Katsevich |
| 2007/0019776 A1 * | 1/2007 | Bontus et al. .................. 378/4 |
| 2007/0140410 A1 * | 6/2007 | Van Stevendaal et al. ...... 378/7 |
| 2007/0253528 A1 * | 11/2007 | Ning et al. ................... 378/15 |

OTHER PUBLICATIONS

Katsevich, A.; Image reconstruction for the circle and line trajectory; 2004; Phys. Med. Biol.; 49:5059-5072.

* cited by examiner

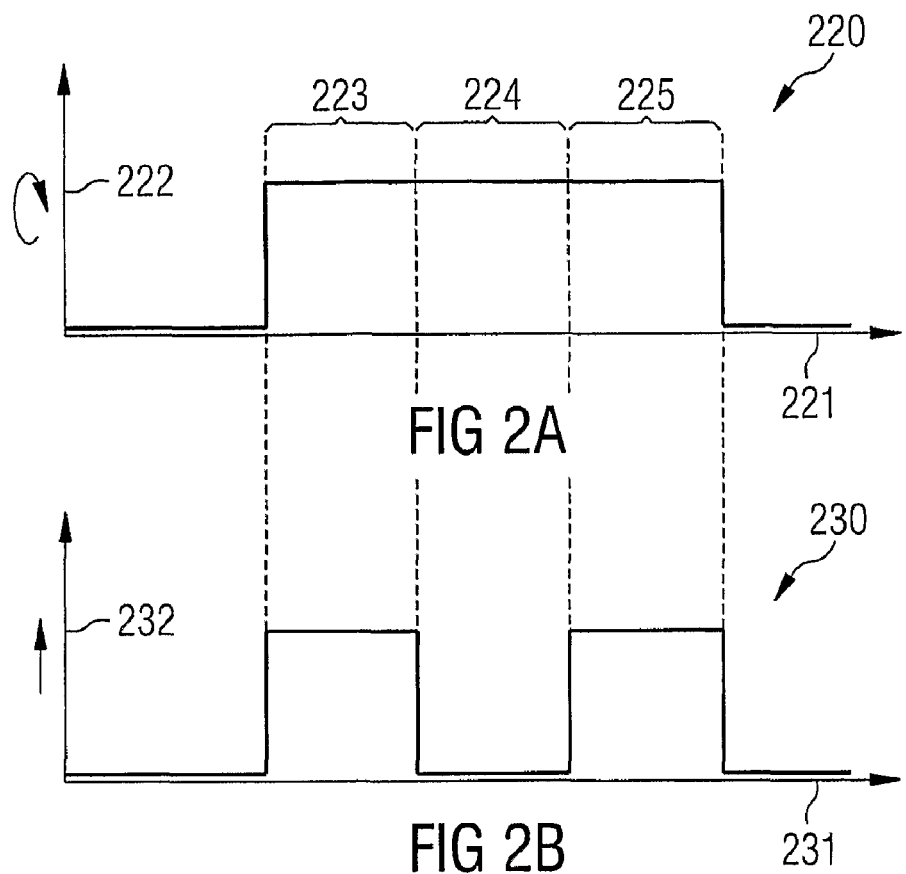
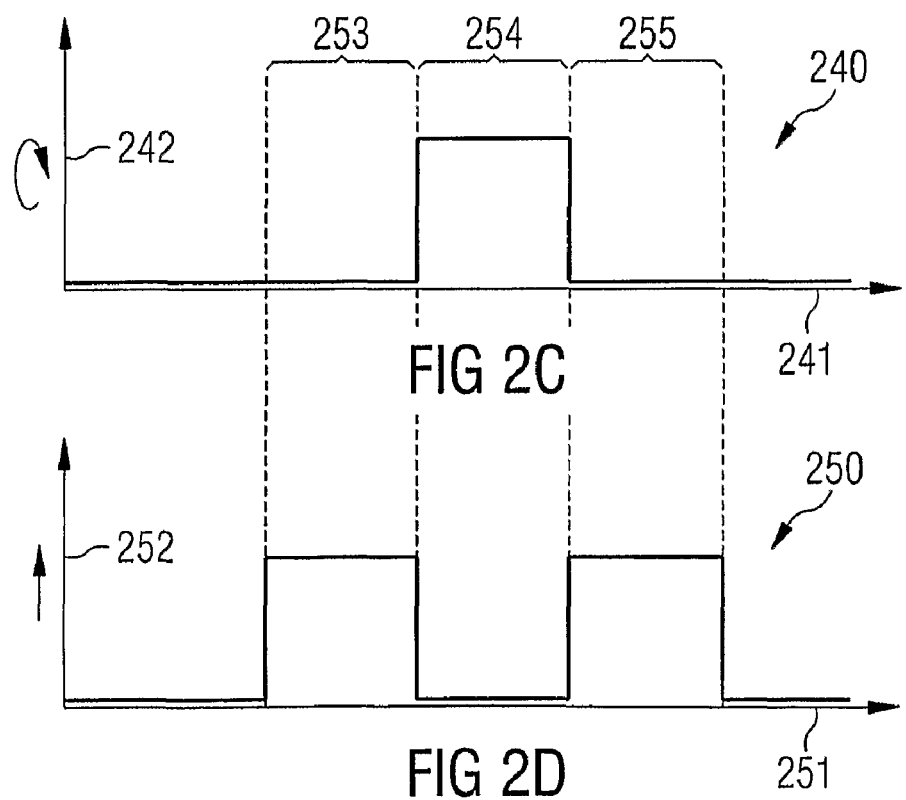

CONE BEAM COMPUTED TOMOGRAPHY WITH MULTIPLE PARTIAL SCANNING TRAJECTORIES

The invention relates to the field of X-ray imaging. In particular, the invention relates to a computer tomography apparatus, to a method of examining an object of interest, to a computer-readable medium and to a program element.

Over the past several years, X-ray baggage inspections have evolved from simple X-ray imaging systems that were completely dependent on an interaction by an operator to more sophisticated automatic systems that can automatically recognize certain types of materials and trigger an alarm in the presence of dangerous materials. An inspection system has employed an X-ray radiation source for emitting X-rays which are transmitted through or scattered from the examined package to a detector.

Computed tomography (CT) is a process of using digital processing to generate a three-dimensional image of the internals of an object from a series of two-dimensional X-ray projections taken around a single axis of rotation. The reconstruction of CT images can be done by applying appropriate algorithms.

Conventionally, an X-ray source and a detector are mounted on a gantry and are rotated around an object of interest in, e.g., a helical manner.

Following the trend of an increasing number of detector rows, circular computer tomography is getting more and more attractive. According to circular computer tomography, an X-ray source and a detector are mounted on a gantry and are rotated around an object of interest in a circular manner. When the detector area of a multi-row detector is large enough to cover the complete object of interest, circular scanning becomes more and more attractive compared to a helical scan as performed in many today's available computer tomography apparatuses.

However, a cone-beam reconstruction of a circular scan may introduce undesired artefacts in the reconstructed image due to the fact that the measured data are mathematically incomplete. Particularly, circular CT tends to show artefacts for slices relatively far-off the center. A reason for these artefacts is the mathematically incomplete trajectory of a circular scan, that is to say data are missing which would be needed for a more accurate reconstruction. It is unlikely that a reconstruction algorithm could ever overcome this problem.

There is a need for an imaging system in which artefacts are efficiently suppressed.

This may be achieved by a computer tomography apparatus, by a method of examining an object of interest, by a computer-readable medium and by a program element with the features according to the independent claims.

According to an exemplary embodiment of the invention, a computer tomography apparatus for examination of an object of interest is provided, wherein the computer tomography apparatus comprises an electromagnetic radiation source adapted to emit electromagnetic radiation to an object of interest, and a detecting device adapted to detect electromagnetic radiation generated by the electromagnetic radiation source and passed through the object of interest. A motion generation device is adapted to move the electromagnetic radiation source and the detecting device with respect to the object of interest along a first trajectory and along a second trajectory which differs from the first trajectory. The second trajectory is selected in such a manner that electromagnetic radiation detected during performing the second trajectory provides data which complete mathematically incomplete data detected during performing the first trajectory to thereby allow a reconstruction of structural information concerning the object of interest.

According to another exemplary embodiment of the invention, a method of examining an object of interest is provided which comprises the steps of emitting electromagnetic radiation to an object of interest by an electromagnetic radiation source, detecting, by a detecting device, electromagnetic radiation generated by the electromagnetic radiation source and passed through the object of interest, and moving the electromagnetic radiation source and the detecting device with respect to the object of interest along a first trajectory and along a second trajectory which differs from the first trajectory, wherein the second trajectory is selected in such a manner that electromagnetic radiation detected during performing the second trajectory provides data which complete mathematically incomplete data detected during performing the first trajectory to thereby allow a reconstruction of structural information concerning the object of interest.

According to still another exemplary embodiment of the invention, a computer-readable medium is provided, in which a computer program of examining an object of interest is stored which, when being executed by a processor, is adapted to carry out the above-mentioned method steps.

According to yet another exemplary embodiment of the invention, a program element of examining an object of interest is provided, which, when being executed by a processor, is adapted to carry out the above-mentioned method steps.

The system of the invention can be realized by a computer program, i.e. by software, or by using one or more special electronic optimization circuits, i.e. in hardware, or in hybrid form, i.e. by means of software components and hardware components. The computer-readable medium and the program element may be implemented in a control system for controlling a computer tomography apparatus.

The characterizing features according to the invention particularly have the advantage that a new motion or trajectory scheme in the frame of computed tomography is provided in which a first and a second trajectory define the motion of different components of a CT apparatus, particularly between an electromagnetic radiation source and detection elements on the one hand and an object under investigation on the other hand. Instead of being restricted to a single kind of trajectory (like a helical motion or a circular motion) the invention extends the functionality by teaching a trajectory which is defined by two different mathematical functions (or two different geometrical paths) which the components undergo in a first time interval and in a second time interval. This allows to use at least two trajectory components each of which, when taken alone (for instance a circular trajectory), only provides mathematically incomplete data, since the data measured during a single of the at least two trajectories are not sufficient to unambiguously reconstruct an image of an object of interest without producing artefacts. However, these missing data are provided by the other trajectory which may be selected to provide complementary data. In other words, the missing data which are needed for a high-quality reconstruction, are acquired when performing the additional second trajectory which allows to mathematically complete the set of data.

According to the invention, it is possible to use either a single second trajectory or a plurality of different or identical second trajectories.

For instance, a circular trajectory allows a very fast investigation of an object of interest with relatively low effort, however may produce artefacts in the reconstructed image which originate from the fact that the data acquired during a pure circular scan do not contain sufficient information for an artefact-free reconstruction of an image of an object under observation. When such a circular scan (or a helical scan which is acquired during a relatively short radiation time) is combined with data acquired before and/or after acquiring data related to the circular scan (or the short helical scan), data from this additional trajectory are combined with data from the main trajectory to reconstruct an image of the object under investigation with high resolution, yielding an image with reduced artefacts.

According to one embodiment of the invention, a circular CT scan with tube and detector moving circularly around the object can be combined with a scan along a line parallel to an axis along which the object of interest extends with tube and detector being free from a rotation. Thus, according to this embodiment, data are used which are acquired on a circular trajectory together with data from a line parallel to a particular linear axis. An advantage of such a procedure is that the described trajectory can be realized with today's scanners.

The data according to a motion of the object of interest along a line can be obtained, in the frame of this exemplary embodiment, for instance during an initial pilot-scan preceding a subsequent circular or helical scan. A pilot-scan (also denoted as a CT scout view or scannogram or topogram) produces a flat image like a plane radiograph to produce this image, the X-ray tube does not rotate while the patient is moved through the scanner. This form of imaging can also be used as a means for obtaining planar images. In other words, during a pilot-scan, the gantry of a computer tomography apparatus does not rotate and X-ray source and X-ray detector are shifted along a length of an object of interest under investigation. A pilot-scan is usually used by a radiologist to identify an organ of interest from a two-dimensional picture scan acquired during the pilot scan, to determine manually in which region a more detailed scan might be carried out.

An investigation including a trajectory comprising of a first trajectory being a circular CT trajectory and a second trajectory being described by a line parallel to a linear axis, can be evaluated with an advantageous reconstruction algorithm. Advantageously, a filtered back-projection method can be used. Using such an algorithm, a significant improvement of the image quality can be obtained, as can be seen by comparing images with or without using a filtered back-projection method.

According to an alternative embodiment of the invention, a combination of a circular trajectory and an "arc" trajectory may be used. In contrast to the above described "circle and line" protocol (in which a low-dose pilot line scan can be used to fill missing radon planes for the reconstruction of the circular scan), the "circle and arc" protocol allows a smoother motion of gantry and mounting table. In the frame of such a circle and arc protocol which allows to move the mounting table smoothly, problems may be avoided which result from the fact that the time between the pilot-scan and the circular scan holds the danger of patient movement, so that stopping the table can change the position of the patient relative to the table in an undesired manner. In the frame of a circle and arc protocol, such problems are securely avoided, since the transition from a line to a circular scan cannot be performed perfectly smoothly, because the gantry has to be accelerated in between. However, the "circle and arc" protocol can be realized as a real and pure one-step protocol. The circle and arc protocol makes it unproblematic for a patient to hold the breath until the scan is over. Thus, for particular applications, the circle and arc protocol may be preferred, for instance when patients can not hold the breath for a long time, a pilot scan was too short, etc.

According to a circle and arc protocol, a gantry may be operated to continuously rotate. The measurement may start with the translation of the table to the position where the circular scan has to be taken, that is to say an arc similar to a helical scan is taken. Then, a pure circular scan may be recorded (during which the table does not move), and after the circular scan, the mounting table may be moved again in the same direction, which again corresponds to an arc-shaped trajectory at the other side of the circle. With such a protocol, which is composed of two arcs and a circle or alternatively of a single arc preceding or succeeding a circle, the data can be acquired in a real one-step acquisition scheme. This reduces artefacts due to motion and inhibits problems with, for instance, a too short pilot-scan, and simultaneously guarantees the same amount of data for every scan. Similar to a line scan, which can be a low-dose pilot-scan, an arc scan can be performed with a smaller current or less dose than the "main" circular scan. The circle and arc protocol is a one-step protocol that guarantees a minimum of motion artefacts, that guarantees a constant amount of data for the reconstruction, and that achieves a high-quality image.

Referring to the dependent claims, further exemplary embodiments of the invention will be described.

In the following, exemplary embodiments of the computer tomography apparatus of the invention will be described. However, these embodiments apply also for the method of examining an object of interest, for the computer-readable medium and for the program element.

According to one embodiment of the computer tomography apparatus, the motion generation device may be adapted in such a manner that the first trajectory precedes the second trajectory. Alternatively, the first trajectory may succeed the second trajectory. According to these embodiments, the two trajectories are acquired one after another, so that two different mathematical functions or geometrical shapes are capable of describing the entire trajectory sequence. The transition between the first and the second trajectory should be smoothly, for instance mathematically continuously, to prevent or avoid any abrupt transition which may be a source of motion artefacts.

Alternatively to the described embodiments, the motion generation device may be adapted in such a manner that the second trajectory comprises a first portion preceding the first trajectory and a second portion succeeding the first trajectory. According to this embodiment, the first trajectory is sandwiched between a first portion of the second trajectory and a second portion of the second trajectory, wherein the two portions of the second trajectory may or may not be identical or symmetrical or mirror-inverted. For instance, a circular trajectory as the first trajectory may be sandwiched by two linear trajectory portions, or two helical or arc-shaped trajectory portions or one linear and one helical or arc-shaped trajectory portion forming the second trajectory. A lot of varieties of the array of trajectories and trajectory portions are possible, however the additional second trajectory should be such that it provides the missing data which remove or eliminate artefacts which may occur from analyzing the first trajectory in an isolated manner.

The motion generation device may be adapted in such a manner that the first trajectory is at least a portion of a circular or a helical trajectory. Particularly, when the first trajectory is a circular trajectory, a very fast scan is possible to cover the entire object of interest. However, missing data yielding image artefacts may be removed by carrying out a reconstruction under consideration of data which are received from a second trajectory, which may be a linear trajectory, a circular trajectory or a helical trajectory, or a portion thereof.

The motion generation device of the computer tomography apparatus may be adapted in such a manner that the first trajectory and the second trajectory may be realized in a (mathematically) continuous (single-step or quasi single-step) manner. Such a one-step acquisition has the advantage that motion artefacts resulting from a movement of the object of interest (for instance a human being under examination) can be avoided, since a one-step acquisition scheme acquires the necessary data continuously and thus in a very short time interval, reducing the risk of undesired motion during the data acquisition.

Particularly, the computer tomography apparatus may have the motion generation device adapted in such a manner that the electromagnetic radiation source and the detecting device are rotated during performing the first trajectory and the second trajectory, wherein the object of interest is linearly moved during performing the second trajectory and is fixed during performing the first trajectory. Such a circle and arc protocol comprises a (central) circular motion part, wherein before and/or after this circular motion part, additional data may be taken from an arc-like motion of tube and detector with respect to the object under investigation.

Still referring to the described embodiment, the motion generation device may be adapted in such a manner that the second trajectory comprises a first portion preceding the first trajectory and a second portion succeeding the first trajectory. This configuration has two portions of the second trajectory sandwiching the first trajectory.

Alternatively to the described embodiment, the motion generation device may be adapted in such a manner that the electromagnetic radiation source and the detecting device are rotated during performing the first trajectory and are fixed during performing the second trajectory, wherein the object of interest is linearly moved during performing the second trajectory and is fixed during performing the first trajectory. Such a circle and line scheme includes a circular scan having additionally a portion with a linear motion of the object of interest with respect to source and detector, wherein this additional information is used to complete the set of data required for the reconstruction of a three-dimensional image.

The motion generation device may be adapted in such a manner that the second trajectory is performed during a pilot-scan. A pilot-scan is usually taken in a CT investigation before the actual measurement in order to determine or limit the investigated region of interest to thereby reduce the radiation dose to which the object of interest is exposed during a main scan following the pilot-scan. Data of such a pilot-scan can be advantageously used as a source for completing the data to reconstruct the three-dimensional image.

The computer tomography apparatus of the invention may further comprise a determination unit which is adapted to determine structural information concerning the object of interest based on an analysis of detecting signals received from the detecting device. Such a determining unit may comprise a central processing unit or the like which may be adapted to process the detected data in such a manner that the reconstructed image is calculated. In the context of the invention, a filtered back-projection analysis may be applied as a reconstruction scheme which may comprise the steps of differentiating the detected data, filtering the detected data and back-projecting the detected data. In the frame of such a reconstruction, the trajectory of X-ray tube and detector with respect to the object of interest are defined, the detector shapes implemented are taken under consideration, and the acquired data are processed for reconstructing the image of the object of interest. In the frame of such a reconstruction, which will be described below in detail, the acquired data may first be differentiated, then a filter step with a proper filter function may be carried out, and subsequently a back-projection step may be carried out to calculate the image of the object of interest from the measured data. The back-projection of detected data may include rebinning of detected data into a parallel geometry. This step may be particularly carried out after a filtering step, so that the back-projection can be performed in an efficient way. Taking this measure allows to significantly accelerate the calculation time of reconstructing the image by mathematically modifying the back-projection terms in a manner that numerically costly terms may be eliminated or replaced by numerically less costly terms. Details of this scheme will be described below. The scheme includes a very efficient grouping of the data to obtain a parallel projection from a focus projection.

The computer tomography apparatus may be adapted in such a manner that back-projecting the detected data includes rebinning the detected data into a parallel geometry. In other words, the data may be rebinned in accordance with a parallel detector geometry, as will be described below in more detail.

The computer tomography apparatus may further be adapted so that filtering the detected data includes filtering the detected data along inclined filter lines (see FIG. 13 to FIG. 16).

The motion generation device of the computer tomography apparatus may comprise a rotatable gantry on which the electromagnetic radiation source and the detecting device may be mounted. By such a gantry, a rotating motion of X-ray tube and detector with respect to the object under investigation is achievable.

Further, the motion generation device may comprise a linearly movable mounting device adapted to receive the object of interest. In other words, the object of interest may be arranged on a mounting device and may be shifted in a linear manner, for instance with a constant velocity or in an accelerated manner. This allows to realize even complicated trajectories.

The detecting device may be a single-slice detector. The missing information for reconstructing the image which information is not measured by the simple single-slice detector during the main scan may be provided by the additional trajectory.

Alternatively, the detecting device may be a multi-slice detector. This configuration is particularly advantageous in the frame of a circular CT apparatus, since a multi-slice detector may be configured to collect sufficient information to reconstruct structural information of an object of interest, when being completed by additional information measured during performing the additional trajectory. According to the invention, missing information can be provided from the auxiliary (for instance linear or arc shaped) trajectory which is performed in addition to a main (for instance circular or helical) trajectory.

The computer tomography apparatus according to the invention may be configured as one of the group consisting of a baggage inspection apparatus, a medical application apparatus, a material testing apparatus and a material science analysis apparatus. However, the computer tomography apparatus according to the invention is not restricted to the described applications, any other application may be used as well.

In a preferred embodiment, the determination unit is adapted to filter the detected data using a $1/\sin \gamma$ filter which is known e.g. from "A quasiexact reconstruction algorithm for helical CT using a 3-Pi acquisition", Med. Phys. 30, 2493-2502 (2003) and which will be explained further below. The determination of structural information concerning the object of interest with data which have been filtered with this filter improves the quality of reconstructed images showing the structural information. Furthermore, with filtered detected data, which have been filtered with the 1/sin γ filter, an exact or quasiexact reconstruction method can be performed, which is based on the reconstruction method disclosed in A. Katsevich, "An improved exact filtered backprojection algorithm for spiral computed tomography", Adv. Appl. Math. 32, pp. 681-97.

This leads to a determination of structural information concerning the object of interest with reduced computational expense compared to other exact or quasiexact reconstruction algorithms like radon inversion. Thus, the determination of structural information concerning the object of interest can be performed faster compared to other exact or quasiexact reconstruction algorithms.

In a further preferred embodiment, the motion generation device is adapted in such a manner that the first trajectory is a circular trajectory, wherein the electromagnetic radiation source and detecting device perform a rotational movement with respect to the object of interest about a rotational axis, the detection device is adapted to detect circular detected data during performing the circular trajectory and the determination unit is adapted to filter the circular detected data along filter lines which are parallel to each other. The use of filter lines, which are parallel to each other, for the circular detected data further improves the quality of reconstructed images of the structural information.

The rotational movement of the electromagnetic radiation source and detection device with respect to the object of interest about a rotational axis can be performed with a fixed object of interest, wherein in this case the electromagnetic radiation source and the detection device move, or with a fixed radiation source and a fixed detection device, wherein in this case the object of interest moves.

In a further preferred embodiment the X-ray motion generation device is adapted in such a manner that the first trajectory is a circular trajectory and that the at least one second trajectory is a portion of a helical trajectory, the detection device is adapted to detect circular detected data during performing the circular trajectory and to detect helical detected data during performing the portion of the helical trajectory and the determination unit is adapted to filter the detected data along filter lines, wherein at least a part of the filter lines of the helical detected data are parallel to a tangent of the circular trajectory or to a tangent of the portion of the helical trajectory. The use of filter lines of the helical detected data, which are parallel to a tangent of the circular trajectory or to a tangent of the portion of the helical trajectory, further improves the quality of reconstructed images showing structural information concerning the object of interest, i.e. these images comprise less image artefacts.

The determination unit can be adapted to filter the helical detected data along a first and second set of filter lines defined in claim 27. The use of these filter lines yields reconstructed images having less artefacts than reconstructed images which do not use these filter lines. Thus, the use of these filter lines improve the quality of reconstructed images showing structural information concerning the object of interest. Furthermore, an exact or quasi-exact reconstruction algorithm can easily be applied on these filtered values leading to a determination of structural information concerning the object of interest with a reduced computational load.

The quality of the reconstructed images showing the structural information concerning the object of interest can be further improved by adapting the determination unit to filter the helical detected along the first and second set of filter lines defined in claim 28.

It is preferred that the determination unit is adapted to perform the filtering along the first set of filter lines from left to right and to perform the filtering along the second set of filter lines from right to left. This further improves the quality of the reconstructed images showing the structural information of the object of interest.

The directions "from left to right" and "from right to left" are defined with respect to a virtual planar detector, which will be explained further below.

It is further preferred that the determination unit is adapted to weight and backproject the helical detected data filtered with the first set of filter lines, the helical detected data filtered with the second set of filter lines and the filtered circular detected data. The weighting and backprojection of the filtered values can be performed with low computational expense and yield reconstructed images of the structural information concerning the object of interest comprising still a good quality.

In a further preferred embodiment, the determination unit is adapted to weight filtered circular detected data with one, to weight filtered helical detected data, which have been filtered with the first set of filter lines, with one half and to weight filtered helical detected data, which have been filtered with the second set of filter lines, with one half. This special weighting scheme further improves the quality of the reconstructed images of the reconstructed images concerning the object of interest.

According to claim 32, the determination unit is adapted to ignore helical detected data values whose projections on a virtual planar detector are located in certain regions of the virtual planar detector. The virtual planar detector and these certain regions will be explained further below. The ignored helical data values are redundant data values, i.e. they can be ignored during reconstruction without decreasing the quality of the reconstructed image. Therefore, according to claim 32, the reconstructed images of structural information concerning the object of interest can be determined with reduced computational load.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited:

FIG. 1 shows a computer tomography apparatus according to a first embodiment of the invention, FIG. 2 shows a computer tomography apparatus according to a second embodiment of the invention, FIG. 2A shows a diagram illustrating the time dependence of the rotation state of the gantry shown in FIG. 2 according to a "circle and arc" protocol, FIG. 2B shows a diagram illustrating the time dependence of the translation state of the gantry shown in FIG. 2 according to the "circle and arc" protocol, FIG. 2C shows a diagram illustrating the time dependence of the rotation state of the gantry shown in FIG. 2 according to a "circle and line" protocol, FIG. 2D shows a diagram illustrating the time dependence of the translation state of the gantry shown in FIG. 2 according to the "circle and line" protocol, FIG. 3 shows a source trajectory according to a "circle and arc" protocol, FIG. 4A and FIG. 4B show reconstructed images with and without a filtered back-projection method according to the invention, FIG. 5 shows a focus-detector according to a filtered back-projection method according to invention, FIG. 6 shows a center detector according to a filtered back-projection method according to the invention, FIG. 7 and FIG. 8 show parallel rays parameterized by focus-detector coordinates according to a filtered back-projection method according to the invention, FIG. 9 and FIG. 10 show parallel rays parameterized by center-detector coordinates according to a filtered back-projection method according to the invention, FIG. 11 shows a projection of a circle onto the planar detector according to the invention, FIG. 12 shows a projection of a circle onto the planar detector according to the invention, FIG. 13 and FIG. 14 show filter lines with filter directions from left to right according to a filtered back-projection method according to the invention, FIG. 15 and FIG. 16 show filter lines with filter directions from right to left according to a filtered back-projection method according to the invention.

The illustration in the drawings is schematically. In different drawings, similar or identical elements are provided with the same reference signs.

FIG. 1 shows an exemplary embodiment of a computed tomography scanner system according to the present invention.

With reference to this exemplary embodiment, the present invention will be described for the application in baggage inspection to detect hazardous materials, such as explosives, in items of baggage. However, it should be noted that the present invention is not limited to this application, but may also be applied in the field of medical imaging, or other industrial applications such as material testing.

Figure 1:
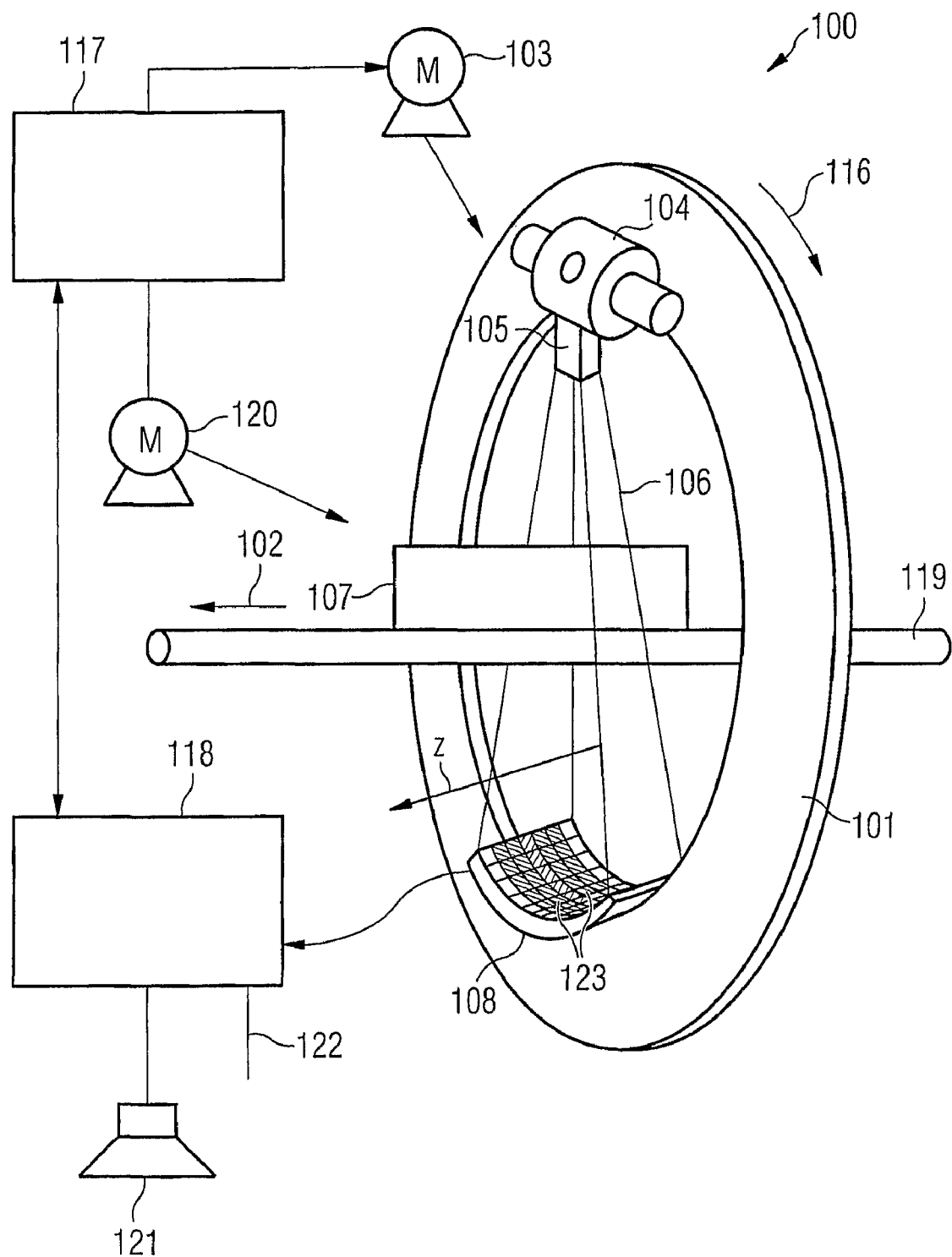

The computer tomography apparatus 100 depicted in FIG. 1 is a cone-beam CT scanner. However, the invention may also be carried out with a fan-beam geometry. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits polychromatic or monochromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the center of the gantry 101, i.e. in an examination region of the CT scanner, and impinges onto the detector 108. As may be taken from FIG. 1, the detector 108 is arranged on the gantry 101 opposite to the main source of radiation 104, such that the surface of the detector 108 is covered by the cone beam 106. The detector 108 depicted in FIG. 1 comprises a plurality of detector elements 123 each capable of detecting, in an energy-resolving manner or in a non-energy-resolving manner, X-rays which have been passed through or scattered by the object of interest 107.

During a scan of the object of interest 107, the source of radiation 104, the aperture system 105 and the detector 108 can be rotated along the gantry 101 in the direction indicated by an arrow 116. For rotation of the gantry 101 with the source of radiation 104, the aperture system 105 and the detector 108, the motor 103 is connected to a motor control unit 117, which is connected to a calculation or determination unit 118.

In FIG. 1, the object of interest 107 is an item of baggage which is disposed on a conveyor belt 119. During the scan of the object of interest 107, while the gantry 101 rotates around the item of baggage 107, the conveyor belt 119 may or may not displace the object of interest 107 along a direction parallel to the rotational axis 102 of the gantry 101. By this, the object of interest 107 can be scanned along a circular scan path (when the conveyor belt 119 does not displace the object of interest 107 and the gantry 101 rotates) or along a helical scan path (when the conveyor belt 119 does displace the object of interest 107 and the gantry 101 rotates) or along a linear scan path (when the conveyor belt 119 does displace the object of interest 107, but the gantry 101 does not rotate). The conveyor belt 119 may be stationary or may move and may also be stopped during the scans to thereby measure signal slices. Instead of providing a conveyor belt 119, for example in medical applications where the object of interest 107 is a patient, a moveable table is used. However, it should be noted that in all of the described cases it is also possible to perform a helical scan, where there is a displacement in a direction parallel to the rotational axis 102, and additionally the rotation of the gantry 101 around the rotational axis 102. Alternatively, in all of the described cases it is also possible to perform a circular scan, where there is no displacement in a direction parallel to the rotational axis 102, but only the rotation of the gantry 101 around the rotational axis 102. Further, it is possible to perform a scan along a linear line, in an accelerated manner or in a constant-velocity manner.

Further, it shall be emphasized that, as an alternative to the cone-beam configuration shown in FIG. 1, the invention can be realized by a fan-beam configuration. In order to generate a primary fan-beam, the aperture system 105 can be configured as a slit collimator.

The detector 108 is connected to the determination unit 118. The determination unit 118 receives the detection result, i.e. the read-outs from the detector elements 123 of the detector 108 and determines a scanning result on the basis of these read-outs. Furthermore, the determination unit 118 communicates with the motor control unit 117 in order to coordinate the movement of the gantry 101 with motors 103 and 120 with the conveyor belt 119.

The determination unit 118 is adapted for reconstructing an image from read-outs of the detector 108. A reconstructed image generated by the calculation unit 118 may be output to a display (not shown in FIG. 1) via an interface 122.

The determination unit 118 may be realized by a data processor to process read-outs from the detector elements 123 of the detector 108.

Furthermore, as may be taken from FIG. 1, the determination unit 118 may be connected to a loudspeaker 121, for example to automatically output an alarm in case of the detection of suspicious material in the item of baggage 107.

The computer tomography apparatus 100 for examination of the object of interest 107 includes the detector 108 having the plurality of detecting elements 123 arranged in a matrix-like manner, each being adapted to detect X-rays passing through the object of interest 107. Further, the computer tomography apparatus 100 comprises the determination unit 118 adapted to determine structural information concerning the object of interest 107 based on an analysis of detecting signals received from the detecting elements 123.

The computer tomography apparatus 100 comprises the X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. Alternatively, not shown in FIG. 1, a slit collimator can be used instead of collimator 105 to produce a fan-beam. The detecting elements 123 form a multi-slice detector array 108. The computer tomography apparatus 100 is configured as a baggage inspection apparatus.

The computer tomography apparatus 100 allows to examine the object of interest 107. The computer tomography apparatus comprises the X-ray tube 104 adapted to emit X-rays on the object of interest 107. The detector 108 is adapted to detect electromagnetic radiation generated by the X-ray tube 104 and passed through the object of interest 107. Further, the gantry 101 and the conveyor belt 119 form a motion generation device (or motion controlling device) which is adapted to move the electromagnetic radiation source 104 and the detector 108 with respect to the object of interest 107 along a first trajectory and along a second trajectory which differs from the first trajectory. The second trajectory is selected in such a manner that electromagnetic radiation detected during performing the second trajectory provides data which complete mathematically incomplete data detected during performing the first trajectory, to thereby allow a reconstruction of structural information concerning the object of interest 107.

The computer tomography apparatus, when being operated according to an embodiment of the invention, first performs a first portion of a first trajectory in which the gantry 101 rotates, wherein simultaneously the conveyor belt 119 linearly moves the object of interest 107 along a direction 102. According to a subsequent second trajectory, the conveyor belt 119 is stopped and the rotation of the gantry 101 is continued. When performing the second trajectory, a circular scan is carried out. In a subsequent second portion of the first trajectory, the conveyor belt 119 moves again along direction 102 so that a second helical like arc is performed as a second trajectory.

The circular scan according to the second trajectory, when taken alone, does not provide a sufficient amount of data for an artefact-free reconstruction of the image of the object of interest 107. However, when the determining unit 118 takes into account also data acquired during the preceding or succeeding arc-like scan, sufficient data are provided to reconstruct the image of the object of interest 107 in an artefact-free manner.

In the following, referring to FIG. 2, a computer tomography apparatus 200 according to a second embodiment of the invention will be described.

The computer tomography apparatus 200 comprises an X-ray tube 201 which irradiates X-rays onto a patient 202 under examination. The X-rays passed through or attenuated by the patient 202 can be detected by a detector 203. The X-ray tube 201 and the X-ray detector 203 are mounted on a rotatable gantry 101 which can be rotated as seen by an arrow 204. Further, the patient 202 is arranged on a mounting table 205 which can be linearly moved along an arrow 206. Data detected by the detector 203 are provided to a determination unit 118 to reconstruct an image of the patient 202.

Two trajectories are used to acquire data concerning the structure of the interior of the patient 202. For performing a first part of a first trajectory, the gantry 101 is fixed and the mounting table 205 is moved with respect to X-ray tube 201 and X-ray detector 203 in a linear manner along the direction 206. In this first portion of the first trajectory, corresponding data are measured. Subsequently, the linear motion of the mounting table 205 is stopped and the gantry 101 is rotated, as described by arrow 204. In this configuration, a circular scan is acquired as a second trajectory. After having finished this circular scan, the rotation of the gantry 101 is stopped again, and the mounting table 205 is shifted again along a direction 206. Thus, a second portion of the first trajectory is acquired. Data measured during performing the two portions of the first trajectory are used to complete the information of data acquired during performing the second trajectory. Thus, the mathematically incomplete set of data measured in correspondence with the second trajectory is completed by data measured during performing the first trajectory so as to allow a reconstruction of the structure of the object of interest 202 in an artefact-free manner.

In the following, referring to FIG. 2A and FIG. 2B, a "circle and arc" protocol will be explained.

Figure 2:
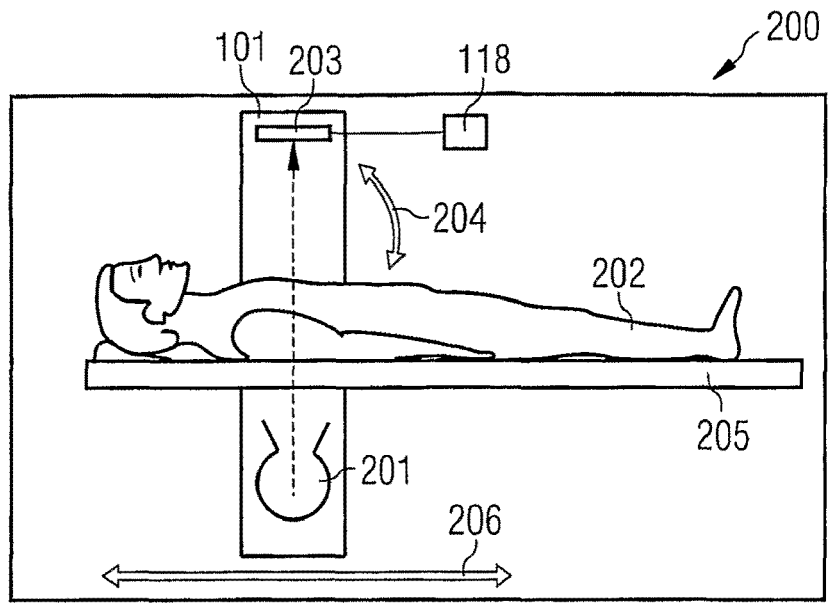

FIG. 2A shows a diagram 220 having an abscissa 221 along which the time is plotted and having an ordinate 222 along which a rotation state of a gantry is plotted. Thus, FIG. 2A illustrates the time dependence of the rotation state of the gantry 101 shown in FIG. 2 according to a "circle and arc" protocol. FIG. 2B shows a diagram 230 having an abscissa 231 along which the time is plotted and having an ordinate 232 along which a linear motion state of a shiftable mounting table is plotted. Thus, FIG. 2B illustrates the time dependence of the translation state of the mounting table 205 shown in FIG. 2 according to a "circle and arc" protocol. During a first portion 223 of a first trajectory, the gantry rotates and the mounting table moves linearly. During a second trajectory 224, the gantry rotates and the mounting table is stopped. During a second portion 225 of the first trajectory, the gantry rotates again and the mounting table again moves linearly. Effectively, the motion trajectory of source 201 and detector 203 with respect to the patient 202 is described by a circular trajectory sandwiched between two arc-shaped trajectories.

In the following, referring to FIG. 2C and FIG. 2D, a "circle and line" protocol will be explained.

FIG. 2C shows a diagram 240 having an abscissa 241 along which the time is plotted and having an ordinate 242 along which a rotation state of a gantry is plotted. Thus, FIG. 2C illustrates the time dependence of the rotation state of the gantry 101 shown in FIG. 2 according to a "circle and line" protocol. FIG. 2D shows a diagram 250 having an abscissa 251 along which the time is plotted and having an ordinate 252 along which a linear motion state of a shiftable mounting table is plotted. Thus, FIG. 2D illustrates the time dependence of the translation state of the mounting table 205 shown in FIG. 2 according to a "circle and line" protocol. During a first portion 253 of a first trajectory, the gantry is fixed and the mounting table moves linearly. During a second trajectory 254, the gantry rotates and the mounting table is stopped. During a second portion 255 of the first trajectory, the gantry is fixed again and the mounting table again moves linearly. Effectively, the motion trajectory of source 201 and detector 203 with respect to the patient 202 is described by a circular trajectory sandwiched between two line-shaped trajectories.

Figure 3:
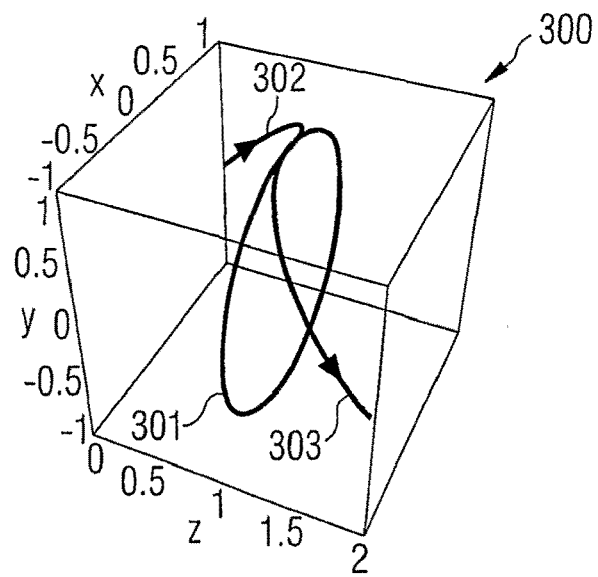

Referring to FIG. 3, a source trajectory 300 is plotted in a three-dimensional manner according to a scan protocol joining two arcs and a circular scan. In other words, the trajectory 300 comprises a central circular trajectory 301 which is preceded by a first arc-like portion 302 of a second trajectory, and which is succeeded by a second arc-like portion 303 of the second trajectory. A scan as the one shown in FIG. 3 can be performed with a continuously rotating gantry in one step. Advantageously, it is relatively insensitive to patient movement and does not require an acceleration or deceleration of the gantry rotation during the scan.

Figure 4A:
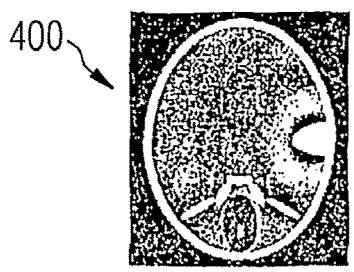
Figure 4B:
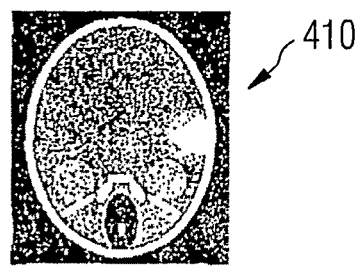

In the following, a reconstruction algorithm according to an exemplary embodiment of the invention will be described. The described reconstruction algorithm is a filtered back-projection method which will be described based on a circle and line scan. Using this algorithm, a significant improvement of the image quality can be achieved, as can be seen by comparing the two images 400, 410 shown in FIG. 4A, FIG. 4B.

In the frame of the filtered back-projection method according to the described embodiment of the invention, a trajectory is considered which comprises a circle, contained in the xy-plane and a line parallel to the z-axis. The latter will be denoted as a z-line. Points on this trajectory sequence can be parameterized according to equation (1):

$$y_0(s) = \begin{pmatrix} R\cos s \\ R\sin s \\ 0 \end{pmatrix}, \quad y_1(z) = \begin{pmatrix} R \\ 0 \\ z \end{pmatrix} \quad (1)$$

In equation (1), R corresponds to the distance from the source to the rotation axis, and s is an angular variable parameterizing the trajectory.

In the following, an analysis of detector shapes will be described.

A conventional CT scanner usually contains a detector, which is part of a cylinder surface. The symmetry axis of this cylinder may be parallel to the z-axis and may contain the focal spot. Points on such a "focus-detector" can be parameterized using an angular variable $\alpha$ and a variable $v_F$. For a source located on the z-line at $z=z_0$, a vector $r_F$ pointing from the origin to the element on the focus-detector is given by equation (2):

$$r_F(\alpha, v_F, z_0) = \begin{pmatrix} R - D\cos\alpha \\ D\sin\alpha \\ z_0 + v_F \end{pmatrix} \quad (2)$$

In equation (2), D corresponds to the distance from the source to the detector-centre.

For convenience, a virtual "center-detector" may be introduced. Similar to the focus-detector, the center-detector is located on the surface of a cylinder. The symmetry axis of the cylinder corresponds to the z-axis, now, such that the points on the detector can be parameterized by introducing a vector $r_C$:

$$r_c(\beta, v_c, z_0) = \begin{pmatrix} -R\cos\beta \\ R\sin\beta \\ z_0 + v_C \end{pmatrix} \quad (3)$$

Figure 5:
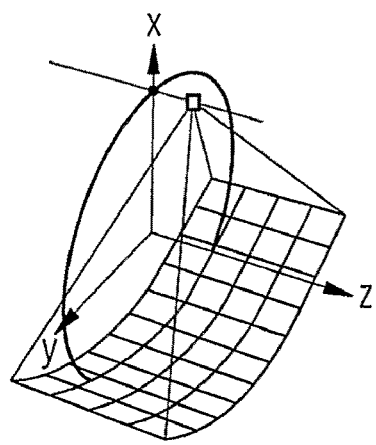
Figure 6:
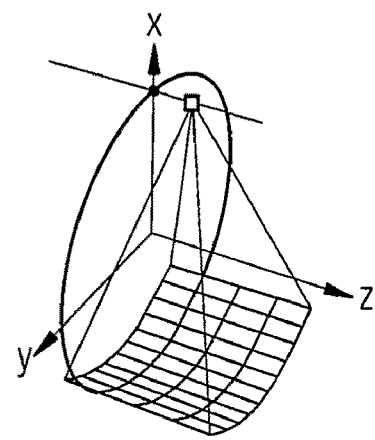

In equation (3), $\beta$ and $v_C$ are detector coordinates in complete analogy to the focus-detector coordinates $\alpha$ and $v_F$. FIG. 5 and FIG. 6 exemplify the trajectory and the focus- and center-detector. Particularly, FIG. 5 shows the focus-detector approach, wherein FIG. 6 shows the center-detector approach.

The line containing the focal spot and a certain focus-detector element can be parameterized as $l_F$, see equation (4):

$$l_F(\alpha, v_F, z_0, \sigma) = \begin{pmatrix} R \\ 0 \\ z_0 \end{pmatrix} + \sigma \begin{pmatrix} -D\cos\alpha \\ D\sin\alpha \\ v_F \end{pmatrix}, \quad 0 \leq \sigma \leq 1 \quad (4)$$

Using equation (4), the coordinates of the detector-element onto which an object point $x=(x, y, z)$ is projected can be computed:

$$\tan\alpha = \frac{y}{R-x} \Rightarrow \sigma = \frac{R-x}{D\cos\alpha} \Rightarrow v_F = \frac{z-z_0}{\sigma} \quad (5)$$

Similarly, the line containing the focal-spot and a center-detector element can be parameterized according to equation (6):

$$l_C(\beta, v_C, z_0, \sigma) = \begin{pmatrix} R \\ 0 \\ z_0 \end{pmatrix} + \sigma \begin{pmatrix} -R(1+\cos\beta) \\ R\sin\beta \\ v_C \end{pmatrix}, \quad 0 \leq \sigma \leq 1 \quad (6)$$

The object-point is projected onto the detector-element with coordinates:

$$\tan\frac{\beta}{2} = \frac{y}{R-x} \Rightarrow \sigma \quad (7)$$
$$= \frac{R-x}{R(1+\cos\beta)}$$
$$= \frac{R-x}{2R\cos^2\frac{\beta}{2}} \Rightarrow v_C$$
$$= \frac{z-z_0}{\sigma}$$

Both, for the focus-detector and center-detector, the coordinates $\alpha$ and $\beta$ depend only on x, y, while $v_F$ and $v_C$ depend on x, y and z.

In the following, an analysis of parallel rays will be described.

A physical detector may comprise columns and rows. The corresponding detector elements may be equidistantly separated in the variables $\alpha$ and $v_F$. Therefore, equations (8) and (9) parameterize the centers of the detector-elements for fixed $z=z_0$:

$$\alpha_k = \alpha_0 + k\Delta\alpha, \, k=0, \ldots, \text{\# columns}-1 \quad (8)$$

$$v_{F_p} = v_{F_0} + P\Delta v_F, \, p=0, \ldots, \text{\# rows}-1 \quad (9)$$

For mathematical reasons, it may be convenient to reorganize the data taken along the z-line, before the back-projection is performed. For projection data associated with a parallel-detector, data from different source-positions may be combined. Using center-detector coordinates, the parameterization of the coordinates in parallel-geometry is given, for a fixed $v_C$, by equations (10), (11):

$$\beta_k = \beta_0 + k\Delta\beta, \, k=0, \ldots, \text{\# columns}-1 \quad (10)$$

$$z_{0,p} = z_{0,min} + p\Delta z, \quad p = 0, \ldots, \# \text{ projections} - 1 \quad (11)$$

Figure 7:
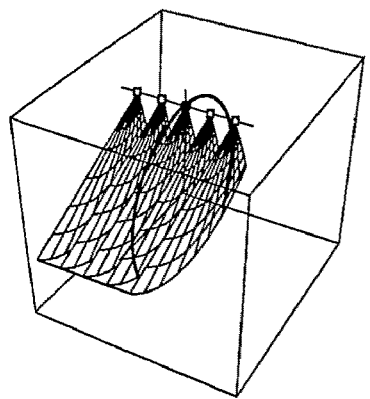
Figure 8:
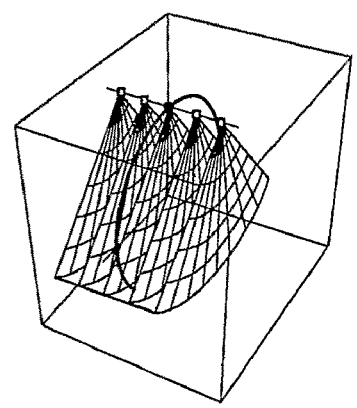
Figure 9:
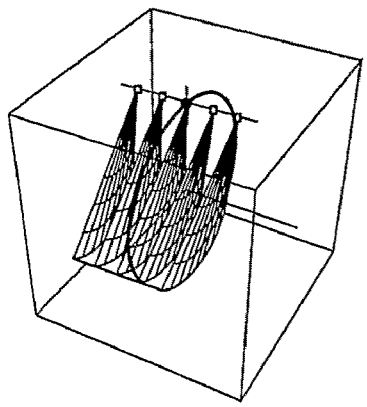
Figure 10:
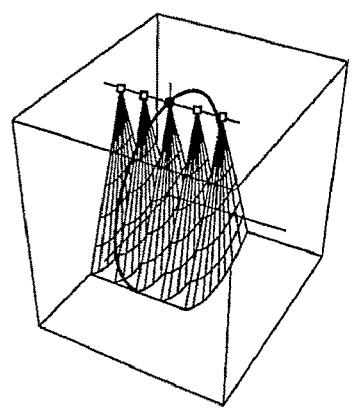

In equations (10) and (11), $\Delta z$ corresponds to the distance between two successive projections on the trajectory-line. FIG. 7 to FIG. 10 each exemplify two parallel projections, for the focus-detector and for the centre-detector, respectively. Particularly, FIG. 7 and FIG. 8 show parallel rays parameterized by focus-detector coordinates. FIG. 9, FIG. 10 show parallel rays parameterized by center-detector coordinates.

Since $v_C$ is fixed for a given parallel-projection, equation (7) can be used in order to determine the detector-column and the detector-row onto which a given object point $x = (x, y, z)$ is projected. For this, $\beta$ and $\sigma$ are first computed, and then these values are used in order to determine $z_0 = z - \sigma v_C$.

In the following, an analysis of a reconstruction scheme will be illustrated.

For every position y on the trajectory, the measured projection data $D_f$ can be described by equation (12):

$$D_f(y, \Theta) = \int_0^\infty dl f(y + l\Theta) \quad (12)$$

In other words, from every position y, line integrals along rays are considered pointing onto a certain set of directions described by different unit vectors $\theta$. For convenience, it is set for the z-line $y_l(s) = y_L(z = hs)$, where $h > 0$ is an arbitrary constant.

A first reconstruction step consists of differentiating the data as follows:

$$D'_f(y(s), \Theta) = \frac{\partial D_f(y(s), \Theta = const.)}{\partial s} \quad (13)$$

In other words, equation (13) means the data are taken from different projections associated with parallel rays which are to be considered. The differentiation step of equation (13) can, for instance, be performed using a Fourier filter. Next, the data are filtered using a $1/\sin \gamma$ filter. For this, the filter directions are determined first. They depend on the position of the focal-spot and on the point onto which the object-point to be reconstructed is projected. Denoting the position of the object-point as x, equation (14) defines the unit vector b:

$$b(s, x) = \frac{x - y(s)}{|x - y(s)|} \quad (14)$$

That is to say, b points from the source to the object-point. The filter directions can be characterized, using unit vectors e, which are perpendicular to b. The relationship between e-vectors and filter-lines is described in the appendix of Bontus, C. et al. "A quasiexact reconstruction algorithm for helical CT using a 3-Pi acquisition", Med. Phys. 30, 2493-2502 (2003). For every s and for every x, there can be one or more filter directions which have to be used. Using b and e, the filtering step can be described by equation (15):

$$P(s, b) = \sum_{q=1}^{N_f} \int_{-\pi}^{\pi} \frac{d\gamma}{\sin \gamma} D'_f(y(s), \cos \gamma b + \sin \gamma e_q) \quad (15)$$

The sum over q in equation (15) is performed, because there can be more than one filter direction. A definition of the vectors e is crucial, for the described embodiment. Once the filtered data have been obtained, the back-projection can be written according to equation (16):

$$f(x) = \frac{(-1)}{2\pi^2} \int_I \frac{ds}{|x - y(s)|} P(s, b(s, x)) \quad (16)$$

Within equation (16), "I" denotes the back-projection interval.

Certainly, the described procedure has to be applied separately to the circular part and to the z-line part of the entire trajectory. In particular, y(s) in equations (13), (15) and (16) corresponds to either $y_0(s)$ or $y_l(s)$. Finally, both results of equation (16) are added up.

In the following, an analysis of back-projection and parallel geometry will be described.

If a rebinning into parallel geometry is performed after the filtering step in equation (15), the back-projection formula of equation (16) changes. In particular, for the circular part, the formula is the same as given in WO 2004/044849 A1. For the z-line part, the back-projection has to be formed via equation (17):

$$f(x) = \frac{(-1)}{2\pi^2} \frac{1}{h} \int dv_F \frac{\cos \lambda}{R} P(v_F, b(v_F, x)) \quad (17)$$

if the parallel data are parameterized by focus-detector coordinates, and via $$f(x) = \frac{(-1)}{2\pi^2} \frac{1}{h} \int dv_C \frac{\cos \lambda}{l} P(v_C, b(v_C, x)), \quad l = 2R \cos \beta \quad (18)$$

if the parallel data are parameterized by center-detector coordinates. In these equations, h was introduced above, when defining $y_l(s) = y_L(z = hs)$, and $\lambda$ corresponds to the cone-angle of a particular ray. The value of $\lambda$ can be computed using equation (19):

$$\tan \lambda = \frac{v_F}{D} = \frac{v_C}{l} \quad (19)$$

An advantage of equations (17) and (18) compared with equation (16) is that no object-point dependent factor $|x-y|$ needs to be computed. This significantly reduces the calculation time by reducing the computational burden for calculating a reconstructed image. The filtered data have to be multiplied only with factors depending on the detector coordinates $\alpha$, $\beta$, $v_F$ or $v_C$.

In the following, an analysis of filter-lines for the circular part will be described.

As described in the above-mentioned reference Bontus, C. et al, "A quasiexact reconstruction algorithm for helical CT using a 3-Pi acquisition", Med-Phys. 30, 2493-2502 (2003), it may be advantageous to introduce a virtual plane detector containing the rotation axis. Coordinates on this detector are denoted as $u_{PL}$ and $v_{PL}$ and the $v_{PL}$-axis is parallel to the z-axis. A line is considered containing the source and being perpendicular to the plane detector. The point ($u_{PL}=0$, $v_{PL}=0$)

corresponds to the point in which this line intersects with the planar detector. Now, each filter line can be described according to equation (20):

$$v_{Pl}(u_{Pl}) = v_0 + \sigma u_{Pl} \qquad (20)$$

In other words, it corresponds to a straight line on the planar detector. In general, the gradient σ is different for different filter-lines.

For the described algorithm, the data obtained are filtered on the circular part along lines parallel to the $u_{PL}$-axis, that is to say $v_{PL}(u_{PL}) = v_0$. The different lines are parameterized by $v_0$. The filter direction goes from left to right.

In the following, an analysis of the filter-lines for the z-line part will be described.

For the parameterization of the filter-lines for the z-line part, it is first considered the projection of the circle onto the planar detector as seen from a source at $z=z_0$. In particular, this projection can be described as $$v_{Pl}(u_{Pl}) = -\frac{z_0}{2}\left[1 + \left(\frac{u_{Pl}}{R}\right)^2\right] \qquad (21)$$

Figure 11:
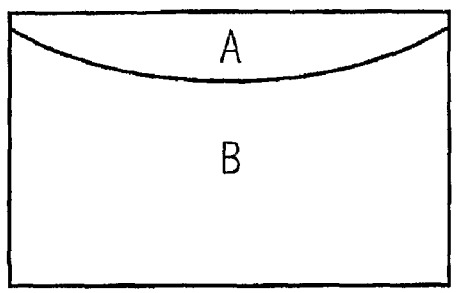
Figure 12:
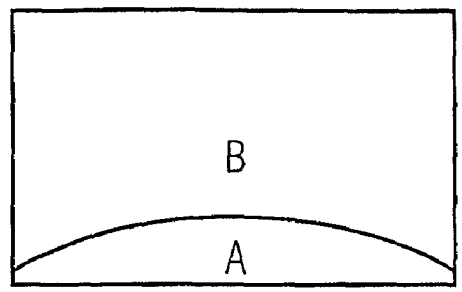

FIG. 11 and FIG. 12 show the projections of the circle for two different $z_0$. Particularly, FIG. 11 shows a projection of the circle onto the planar detector seen from $z_0 < 0$. FIG. 12 shows a projection of the circle onto the planar detector seen from $z_0 > 0$. The detector area is divided into two regions A and B as shown in FIG. 11 and FIG. 12. If the object-point is projected into region A, the projection data associated with a current source position is not used for the reconstruction. Therefore, the data in region A should be set to zero. For region B, the filter lines may be defined in the following.

A line tangential to be projected circle can be parameterized using equation (22):

$$v_{Pl}(u_{Pl}) = -\frac{z_0}{2}\left[1 + \left(\frac{u_0}{R}\right)^2\right] - \frac{z_0 u_0}{R^2}(u_{Pl} - u_0) \qquad (22)$$

In equation (22), $u_0$ is the coordinate at which the line is tangential. In particular, if one looks for the tangential line containing the point $(u_1, v_1)$, the parameter $u_0$ can be computed according to equation (23):

$$u_0 = u_1 \pm \sqrt{u_1^2 + R^2\left(1 + 2\frac{v_1}{z_0}\right)} \qquad (23)$$

The sign in front of the square-root has to be chosen depending on, if the tangential point is desired to be located left (minus) or right (plus) of $(u_1, v_1)$.

Figure 13:
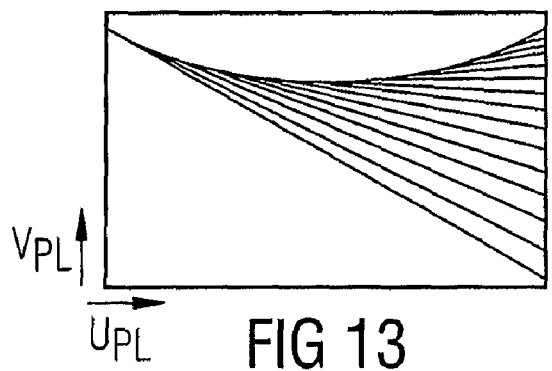
Figure 14:
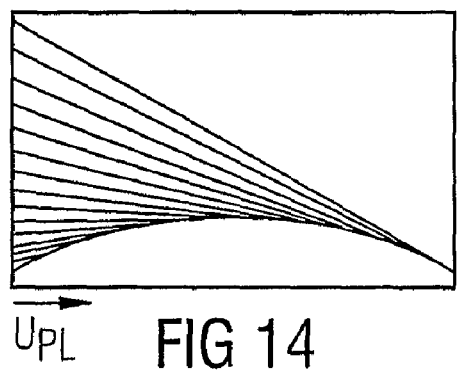
Figure 15:
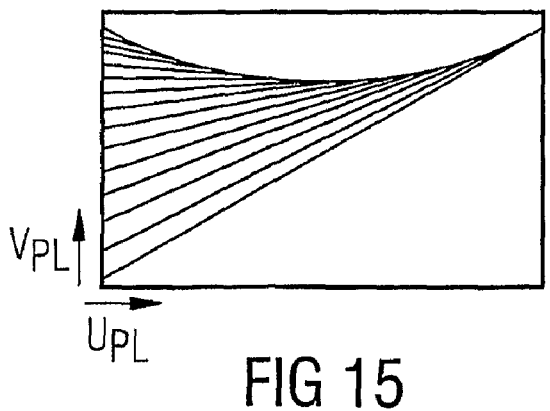
Figure 16:
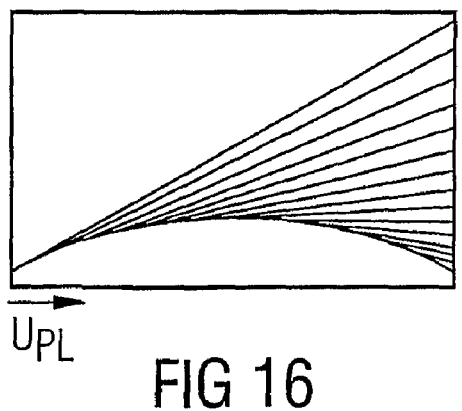

Now, the filter-lines are sets of lines which are tangential on the projected circle. FIG. 13 to FIG. 16 exemplify these lines. FIG. 13, FIG. 14 show filter lines with different filter directions from left to right. FIG. 15, FIG. 16 show filter lines with filter directions from right to left. In particular, for each point $(u_{PL}, v_{PL})$, the contributions of two different filter-lines are used. For the first one, the tangential point is on the left, for the second one it is on the right of $(u_{PL}, v_{PL})$. The direction of filtering depends on $z_0$. If $z_0 < 0$, the filtering goes from left to right, if the tangential point is on the left, while it goes from right to left, if the tangential point is on the right. If $z_0 > 0$, the filtering goes from left to right, if the tangential point is on the right, while it goes from right to left, if the tangential point is on the left. FIG. 13 to FIG. 16 illustrates this.

The filter lines shown in FIG. 13 to FIG. 16 cover only part of the detector. Trying to cover a larger part would necessarily result in an extrapolation, since the filter-lines would become very steep. In any case, only data from regions for which two filter-lines are defined, should be used for the back-projection.

In the following, a further embodiment according to the invention will be described.

The computer tomography apparatus of the further embodiment is similar to the computer tomography apparatus depicted in FIG. 1. That is, it is a cone-beam CT scanner 100 comprising a gantry 101, which is rotatable around a rotational axis 102. The gantry 101 is driven by means of a motor 103. Reference numeral 104 designates a source of radiation such as an X-ray source, which, according to an aspect of the present invention, emits polychromatic or monochromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the center of the gantry 101, i.e. in an examination region of the CT scanner, and impinges onto the detector 108. As may be taken from FIG. 1, the detector 108 is arranged on the gantry 101 opposite to the main source of radiation 104, such that the surface of the detector 108 is covered by the cone beam 106. The detector 108 depicted in FIG. 1 comprises a plurality of detector elements 123 each capable of detecting, in an energy-resolving manner or in a non-energy-resolving manner, X-rays which have been passed through or scattered by the object of interest 107.

During a scan of the object of interest 107, the source of radiation 104, the aperture system 105 and the detector 108 can be rotated along the gantry 101 in the direction indicated by the arrow 116. For rotation of the gantry 101 with the source of radiation 104, the aperture system 105 and the detector 108, the motor 103 is connected to a motor control unit 117, which is connected to a determination unit 118.

In FIG. 1, the object of interest 107 is an item of baggage which is disposed on a conveyor belt 119. During the scan of the object of interest 107, while the gantry 101 rotates around the item of baggage 107, the conveyor belt 119 may or may not displace the object of interest 107 along a direction parallel to the rotational axis 102 of the gantry 101. By this, the object of interest 107 can be scanned along a circular scan path (when the conveyor belt 119 does not displace the object of interest 107 and the gantry 101 rotates) or along a helical scan path (when the conveyor belt 119 does displace the object of interest 107 and the gantry 101 rotates). The conveyor belt 119 may be stationary or may move and may also be stopped during the scans to thereby measure signal slices. Instead of providing a conveyor belt 119, for example in medical applications where the object of interest 107 is a patient, a moveable table can be used.

The detector 108 is connected to the determination unit 118. The determination unit 118 receives the detection result, i.e. the read-outs from the detector elements 123 of the detector 108 and determines a scanning result on the basis of these read-outs. Furthermore, the determination unit 118 communicates with the motor control unit 117 in order to coordinate the movement of the gantry 101 with motors 103 and 120 with the conveyor belt 119.

The determination unit 118 is adapted for reconstructing an image from read-outs of the detector 108. A reconstructed image generated by the determination unit 118 may be output to a display (not shown in FIG. 1) via an interface 122.

The determination unit 118 may be realized by a data processor to process read-outs from the detector elements 123 of the detector 108.

The computer tomography apparatus 100 for examination of the object of interest 107 includes the detector 108 having the plurality of detecting elements 123 arranged in a matrix-like manner, each being adapted to detect X-rays passing through the object of interest 107. Further, the computer tomography apparatus 100 comprises the determination unit 118 adapted to determine structural information concerning the object of interest 107 based on an analysis of detecting signals received from the detecting elements 123.

The computer tomography apparatus 100 comprises the X-ray source 104 adapted to emit X-rays to the object of interest 107. The collimator 105 (aperture system) provided between the electromagnetic radiation source 104 and the detecting elements 123 is adapted to collimate an electromagnetic radiation beam emitted from the electromagnetic radiation source 104 to form a cone-beam. The detecting elements 123 form a multi-slice detector array 108. The computer tomography apparatus 100 is configured as a baggage inspection apparatus.

The computer tomography apparatus 100 allows to examine the object of interest 107. The computer tomography apparatus comprises the X-ray tube 104 adapted to emit X-rays on the object of interest 107. The detector 108 is adapted to detect electromagnetic radiation generated by the X-ray tube 104 and passed through the object of interest 107. Further, the gantry 101 and the conveyor belt 119 form a motion generation device (or motion controlling device) which is adapted to move the electromagnetic radiation source 104 and the detector 108 with respect to the object of interest 107 along a first trajectory and along a second trajectory which differs from the first trajectory. The first trajectory is a circular trajectory, and the second trajectory is a portion of a helical trajectory and is selected in such a manner that electromagnetic radiation detected during performing the second trajectory provides data which complete mathematically incomplete data detected during performing the first trajectory, to thereby allow a reconstruction of structural information concerning the object of interest 107. The term "portion of a helical trajectory" includes a helical trajectory having one or more windings and also a smaller portion of a helical trajectory comprising only an arc which is a part of a helical trajectory.

The computer tomography apparatus, when being operated according to this embodiment of the invention, performs the circular and the portion of the helical trajectory in a way that electromagnetic radiation detected during performing the portion of the helical trajectory provides helical detected data which complete mathematically incomplete circular detected data, which has been detected during performing the circular trajectory, to thereby allow a reconstruction of structural information concerning the object of interest 107.

The circular scan, when taken alone, does not provide a sufficient amount of data for an exact or quasiexact reconstruction of the image of the object of interest 107. However, when the determining unit 118 takes also data into account acquired during performing the portion of the helical trajectory, sufficient data are provided for exact or quasiexact reconstruction of the image of the object of interest 107.

Figure 18:
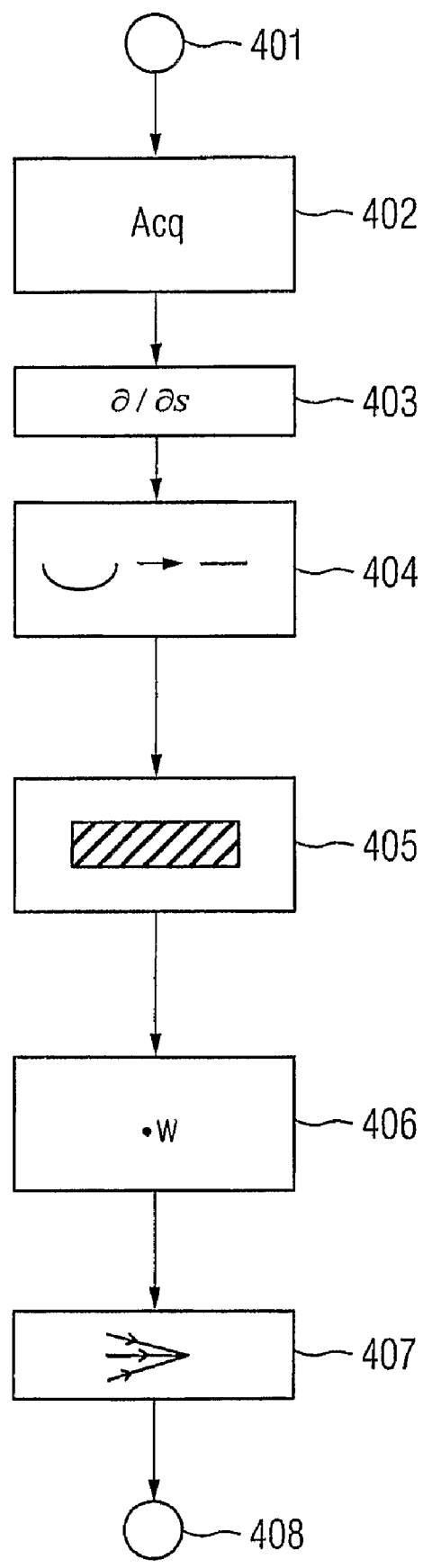
FIG. 18 shows a schematic diagram illustrating a computer tomography method according to the invention.

This embodiment of the computer tomography apparatus is adapted to perform a computer tomography method which will be explained in the following with respect to FIG. 18.

After initialization of the computer tomography apparatus in step 401 data are acquired (step 402).

As already explained above, the computer tomography apparatus performs the circular trajectory 501 (see FIG. 19) and the portion 503 of the helical trajectory in a way that electromagnetic radiation detected during performing the portion 503 of the helical trajectory provides helical detected data which complete mathematically incomplete circular detected data, which have been detected during performing the circular trajectory 501, to thereby allow a reconstruction of structural information concerning the object of interest 107. In particular, firstly, the computer tomography apparatus performs a circular trajectory 501 wherein the X-ray tube is switched on and circular detected data are detected. Then, the X-ray tube is switched off and the conveyor belt or table is moved away from a circular position to a start position, wherein the circular position is the position where the circular scan was performed. Thus, the conveyor belt or table is moved back from the start position, passes the circular position and stops at a stop position. During the movement of the conveyor belt or table, starting at the start position, passing the circular position and stopping at the stop position, the X-ray tube 104 is switched on, and the computer tomography apparatus performs the portion 503 of the helical trajectory. During performing the circular trajectory 501 and the portion 503 of the helical trajectory the gantry is continuously rotating. During the movement of the conveyor belt or table from the start position towards the circular position, the X-ray 104 tube is switched on, when a first detecting element 123 of the detector 108 passes the circular position. The X-ray tube 104 is switched off, when a last detecting element 123 of the detector 108 passes the circular position. This allows for minimized dose applied to the object of interest 107.

Alternatively, after defining a circular position, firstly, the portion 503 of the helical trajectory can be performed and, secondly, the circular trajectory 501 can be performed at the circular position.

During performing the circular trajectory 501 circular detected data and during performing the portion 503 of the helical trajectory helical detected data are acquired.

In this embodiment, the circular position is located at $z_0=0$. Thus, the circular trajectory 501 can be parameterized according to equation (1). The portion 503 of the helical trajectory can be parameterized by following equation:

$$y_\partial(s) = \begin{pmatrix} R\cos s \\ R\sin s \\ \hbar s \end{pmatrix}, \quad (24)$$

wherein $h=2\pi\hbar$ is the pitch of the portion 503 of the helical trajectory.

The determination unit 118 is, in this embodiment, adapted to determine structural information concerning the object of interest 107 using a reconstruction algorithm according to steps 403 to 407.

In step 403 the detected data are differentiated according to equation (13). Thus, detected data values, which correspond to parallel X-rays emanating from different focal spot positions, are differentiated. This differentiation step can be performed using a Fourier transformation. This differentiation is performed separately for the circular trajectory $y_0(s)$ and the portion of the helical trajectory $y_\partial(S)$ and is explained in more detail in Bontus, C. et al, "A quasiexact reconstruction algorithm for helical CT using a 3-Pi acquisition", Med-Phys. 30, 2493-2502 (2003).

Figure 19:
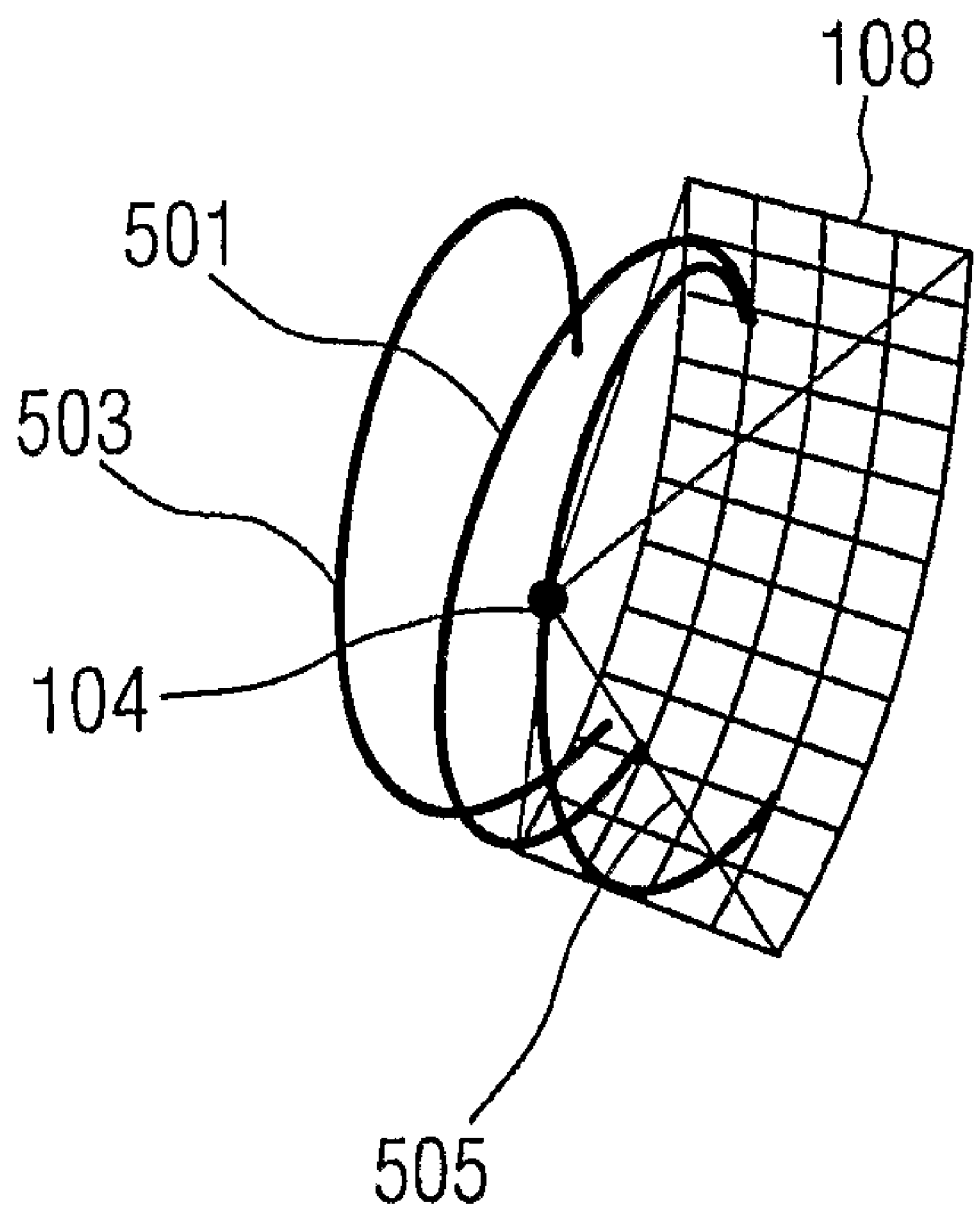
FIG. 19 shows a first trajectory being a circular trajectory and a second trajectory being a portion of a helical trajectory.

In step 404 the above introduced virtual planar detector 605 is defined, which is described in the above-mentioned reference "A quasiexact reconstruction algorithm for helical CT using a 3-Pi acquisition", Bontus, C. et al., Med-Phys. 30, 2493-2502 (2003). Furthermore, the circular 501 and the portion 503 of the helical trajectory are projected along the corresponding X-rays 505, from which only the four outermost X-rays are illustrated in FIG. 19, onto the planar detector 605.

The projection 603 of the circular trajectory 501 and the projections 601a, 601b of the portion 503 of the helical trajectory are shown in FIGS. 20 to 23, seen from a focal spot position on the portion 503 of the helical trajectory. From FIG. 20 to FIG. 22 the focal spot moves on the portion 503 of the helical trajectory, i.e. the projections 603, 601a, 601b are seen from different focal spot positions, wherein in FIG. 20 the focal spot is positioned on one side of the circular position, wherein in FIG. 21 the focal spot is positioned on the same side of, but closer to the circular position, and wherein in FIG. 22 the focal spot is positioned on the other side of the circular position.

Figure 20:
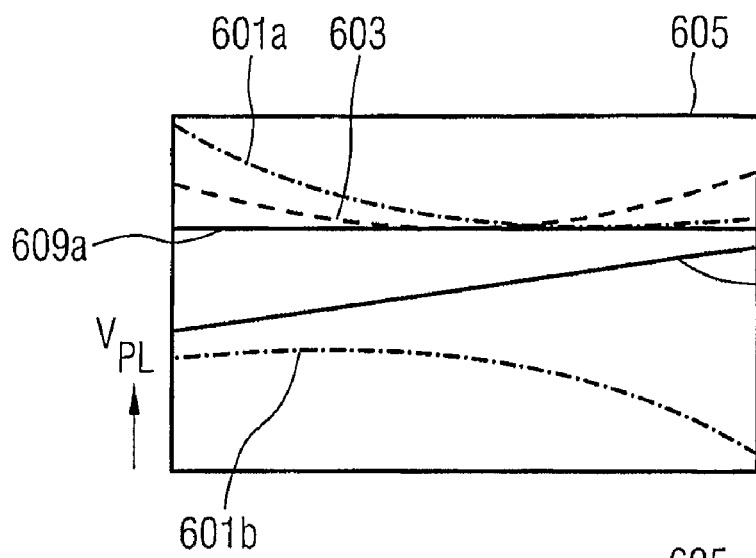
FIGS. 20 to 23 show projections of the trajectories onto the planar detector.
Figure 21:
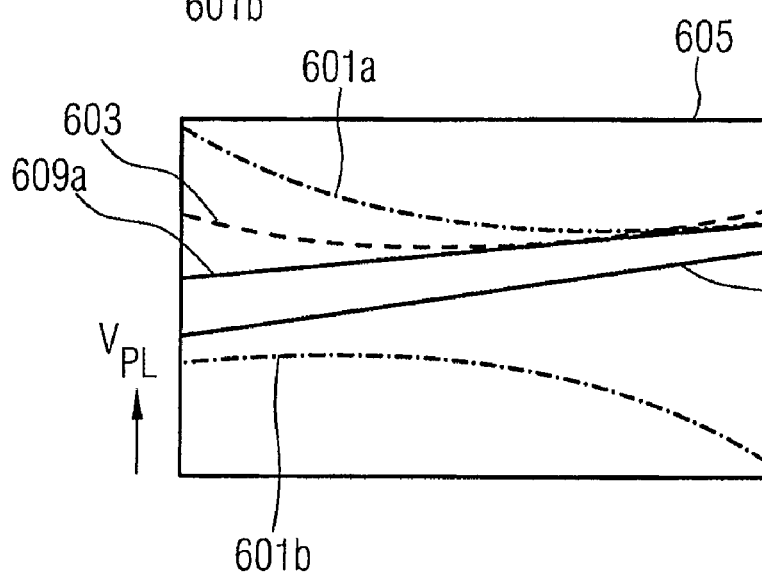
Figure 22:
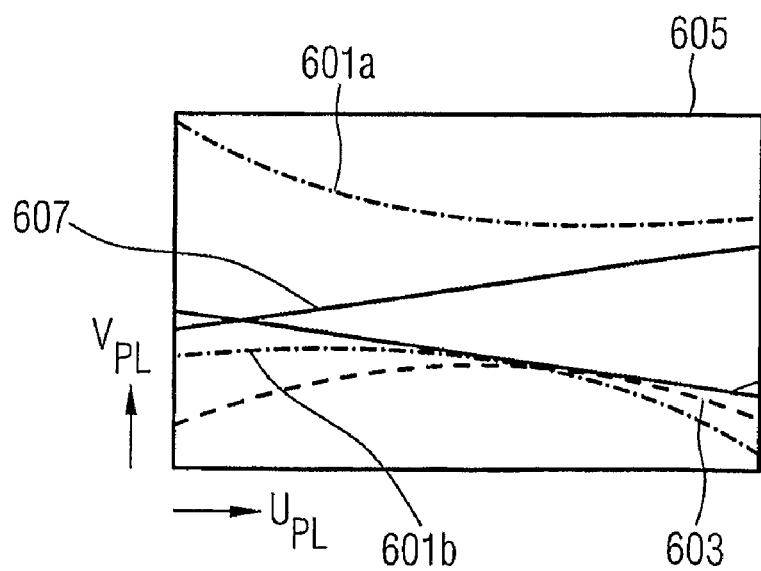

Two windings of the portion 503 of the helical trajectory are projected onto the planar detector 605. Thus, FIGS. 20 to 22 show two projections 601a, 601b of windings of the portion 503 of the helical trajectory 503. The line 603 is the projection of the circular trajectory 501.

The projection 603 of the circular trajectory 501 can be parameterized according to equation (21). The projections 601a, 601b of the windings of the portion 503 of the helical trajectory on the planar detector 605 can be parameterized according to following equation:

$$v_{Pl}^{up,low}(u_{Pl}) = \pm h\left(1 + \left(\frac{u_{Pl}}{R}\right)^2\right)\left(\frac{\pi}{2} \mp \arctan\frac{u_{Pl}}{R}\right), \quad (25)$$

Wherein $v_{P1}^{up}(u_{P1})$ defines the upper projection 601a of the windings of the portion 503 of the helical trajectory and wherein $v_{P1}^{down}(u_{P1})$ defines the lower projection 601b of the windings of the portion 503 of the helical trajectory. The algebraic sign "+" corresponds to $v_{P1}^{up}(u_{P1})$, and the algebraic sign "−" corresponds to the $v_{P1}^{low}(u_{P1})$.

The solid line 607 passes the center of the planar detector 605 and is the asymptote, which has a positive gradient, to the projections 601a, 601b of the portion 503 of the helical trajectory. The solid lines 609a, b are the tangents to the projection 603 of the circular trajectory and to the upper projection 601a and to the lower the projection 601b of the portion 503 of the helical trajectory, respectively, depending on the position of the focal spot relative to the circular position. That is, if the projection 603 of the circular trajectory is located in the upper part of the planar detector 605 (FIGS. 20 and 21, $z_0$<0), the solid line 609a is the tangent to the projection 603 of the circular trajectory and to the upper projection 601a of the portion 503 of the helical trajectory, and if the projection 603 of the circular trajectory is located in the lower part of the planar detector 605 (FIG. 22, $z_0$>0), the solid line 609b is the tangent to the projection 603 of the circular trajectory and the lower projection 601b of the portion 503 of the helical trajectory.

Figure 23:
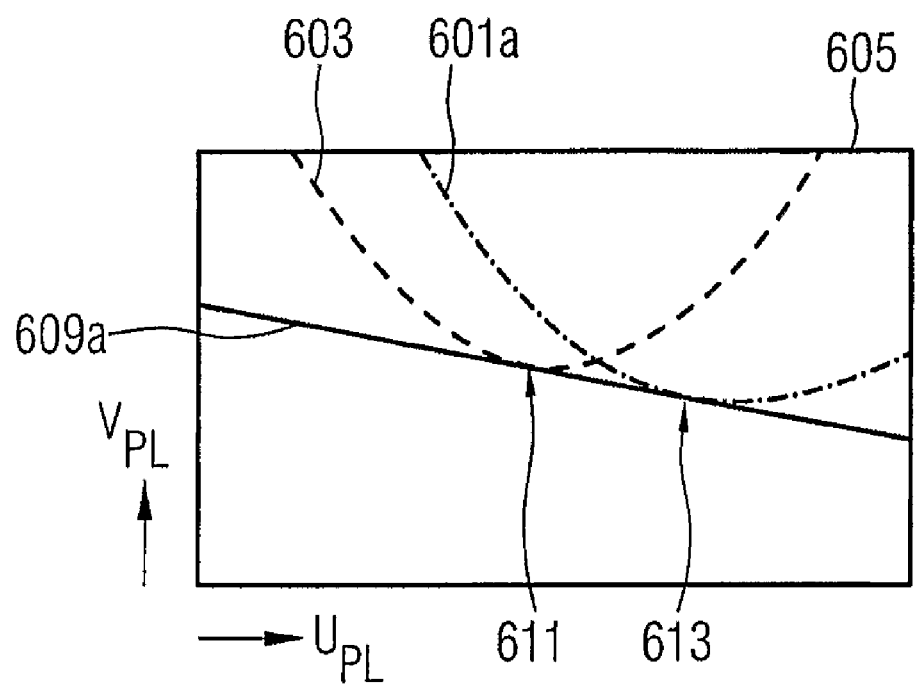

FIG. 23 shows the upper portion of FIG. 20 in larger scale.

The helical detected data values and the circular detected data values are projected onto the planar detector along the corresponding X-rays.

In step 405 the helical detected data and the circular detected data are filtered along filter lines using a 1/sin γ filter.

For this, the filter lines are determined first. They depend on the position of the focal spot and the object point to be reconstructed. Denoting the position of the object-point as x, equation (14) defines the unit vector b. That is to say, b points from the source to the object-point. The filter directions, which are defined as the direction along filter lines, can be characterized, using unit vectors e, which are perpendicular to b. The relationship between e-vectors and filter-lines, and directions along the filter lines, is described in the appendix of "A quasiexact reconstruction algorithm for helical CT using a 3-Pi acquisition", Bontus, C. et al., Med. Phys. 30, 2493-2502 (2003). For every s and for every x, there can be one or more filter directions which have to be used. Using b and e, in this embodiment, the filtering step can be described by equation (26):

$$P(s, b) = \sum_{q=1}^{N_f} \mu_q \int_{-\pi}^{\pi} \frac{d\gamma}{\sin\gamma} D'_f(y(s), \cos\gamma b + \sin\gamma e_q). \quad (26)$$

The sum over q in equation (26) is performed, because there can be more than one filter direction, i.e. more than one filter line and corresponding direction along the filter lines for each detected data value, wherein each detected data value corresponds to a combination of s and b. A definition of the vectors e is crucial, for the described embodiment. Once the filtered data have been obtained, the back-projection can be written according to equation (16).

Certainly, the described procedure has to be applied separately to the circular trajectory 501 and to the portion 503 of the helical trajectory. In particular, y(s) corresponds in this embodiment to either $y_o(s)$ or $y_3(s)$. Finally, the results of equation (16) for the circular trajectory and for the portion of the helical trajectory are added up.

The filter lines of the circular detected data are defined according to equation (20). Thus, the filter lines correspond to straight lines on the planar detector. In general, the gradient σ is different for different filter lines, but in this embodiment the gradient σ is identical for all filter lines of circular detected data, i.e. these filter lines are parallel to each other. Furthermore, in this embodiment, the circular detected data are filtered along filter lines which are parallel to the $u_{P1}$-axis, i.e. $v_{P1}(u_{P1})$=$v_0$. The different filter lines are parameterized by $v_0$.

The filter direction goes from left to right along the respective filter lines in the orientation shown in FIGS. 20 to 27. The orientation refers to a right-handed coordinate system wherein the $u_{P1}$-axis is the first axis, wherein the $v_{P1}$-axis is the second axis and wherein the third axis points in the direction from the center of the planar detector towards the X-ray source. The $u_{P1}$-axis points from left to right. The $v_{P1}$-axis points from the bottom to the top. In this description the terms "left", "right", "above", "below", "positive gradient", "negative gradient" etc. refer to this right-handed coordinate system.

At first, the filter lines and helical detected data, which will be ignored during reconstruction, will be explained with respect to situations in which the focal spot is positioned on the side of the circular position which is illustrated by FIGS. 20, 21, 23, i.e. in which the projection 603 of the circular trajectory is located in the upper part of the virtual planar detector. If the circular position is located at $z_0$=0, these situations illustrated in FIGS. 20, 21, 23 correspond to $z_0$<0.

Helical detected data which are projected onto certain regions on the planar detector are not used for reconstruction and, therefore, not filtered. These regions comprise all points on the planar detector lying above the projection 603 of the circle, all points lying above the upper projection 601a of the portion 501 of the helical trajectory and all points with $u_{P1}$-coordinates between two points of tangency 611, 613 (see FIG. 23) of the tangent 609a, which is tangential to the projection 603 of the circular trajectory 501 and to the upper projection 601a of the portion 503 of the helical trajectory, and which are located above this tangent 609a.

Two sets of filter lines are defined for the helical detected data, i.e. in this embodiment, for helical detected data in equation (26) $N_f$ is equal to 2.

A first set of filter lines for helical detected data is determined as follows. For a helical detected data value whose projection on the planar detector 605 is located below the asymptote 607, the corresponding filter line is parallel to the asymptote 607, i.e. parallel to the derivation $\dot{y}_\partial(s)$ of the portion 503 of the helical trajectory. If the projection of the helical detected data value is located above the asymptote 607, the corresponding filter line is either tangential to the projection 603 of the circular trajectory 501 or tangential to the upper projection 601a of the portion 503 of the helical trajectory, wherein the point of tangency is located on the right-hand side of the location of the projection of the corresponding helical detected value on the planar detector 605. The decision, whether the filter lines are tangential to the projection 603 of the circular trajectory 501 or tangential to the upper projection 601a of the portion 503 of the helical trajectory depends on the gradient of the corresponding tangents. If the gradient of the corresponding tangent of the projection 603 of the circular trajectory 501 is smaller than the tangent of the upper projection 601a of the portion 503 of the helical projection, the filter line is tangential to the projection 603 of the circular trajectory 501. If the gradient of the corresponding tangent of the of the projection 603 circular trajectory 501 is larger than the tangent of the upper projection 601a of the portion 503 of the helical projection, the filter line is tangential to the upper projection 601a of the portion 503 of the helical trajectory.

The respective tangents run through the respective detected data value for which a filter line has to be determined. Thus, the gradient of the respective tangent is defined by the position of the projected helical detected data value on the planar detector.

If gradients are compared, the algebraic sign is considered. Thus, a negative gradient with a larger absolute value is smaller than a negative gradient having a smaller absolute value.

The helical detected data are filtered from the left to the right along the filter lines of the first set of filter lines.

Figures 24, 25:
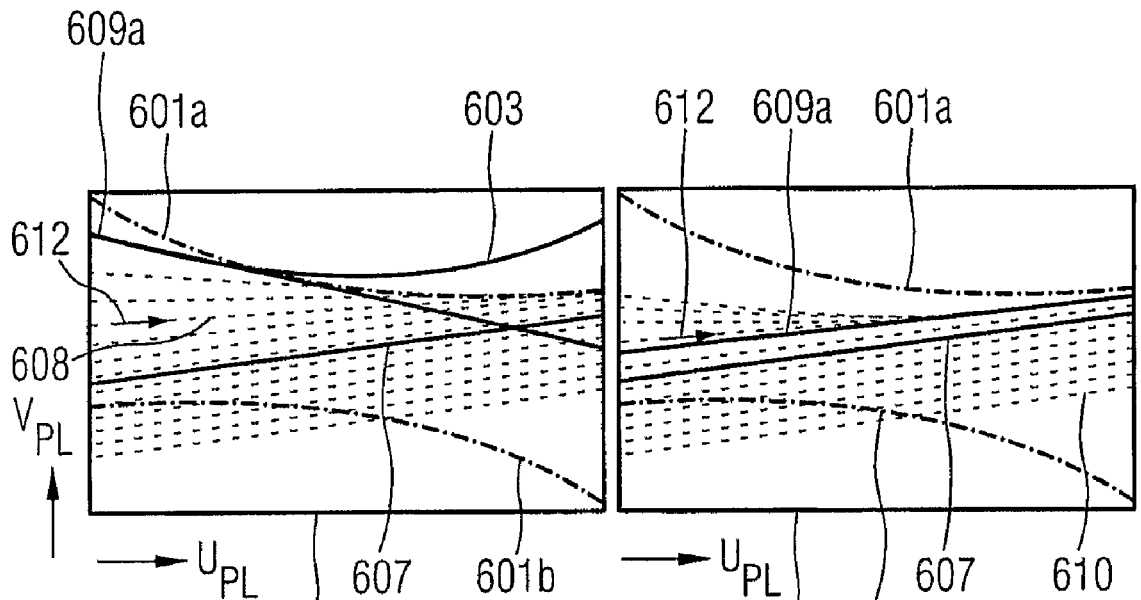
FIGS. 24 to 27 show filter lines on the planar detector.

A first set of filter lines 608, 610 is shown in FIGS. 24 and 25 for two different focal spot positions on the portion of the helical trajectory wherein $z_0$ is negative. The helical detected values, which have been projected onto the virtual planar detector, are filtered along the filter lines 608, 610 from left to right, i.e. along the direction indicated by the arrows 612.

A second set of filter lines is determined as follows. For a helical detected data value which has been projected onto the planar detector 605 the corresponding filter line is either tangential to the projection 603 of the circular trajectory 501 or tangential to the upper projection 601a of the portion 503 of the helical trajectory, wherein the point of tangency is located on the left-hand side of the location of the projection of the corresponding helical detected value on the planar detector 605. The decision, whether the filter lines are tangential to the projection 603 of the circular trajectory 501 or tangential to the upper projection 601a of the portion 503 of the helical trajectory depends on the gradient of the corresponding tangents. If the gradient of the corresponding tangent of the projection 603 of the circular trajectory 501 is smaller than the tangent of the upper projection 601a of the portion 503 of the helical projection, the filter line is tangential to the upper projection 601a of the portion 503 of the helical trajectory. If the gradient of the corresponding tangent of the projection 603 of the circular trajectory 501 is larger than the tangent of the upper projection 601a of the portion 503 of the helical projection, the filter line is tangential to the projection 603 of the circular trajectory 501.

The helical detected data are filtered from the right to the left along the filter lines of the second set of filter lines.

Figures 26, 27:
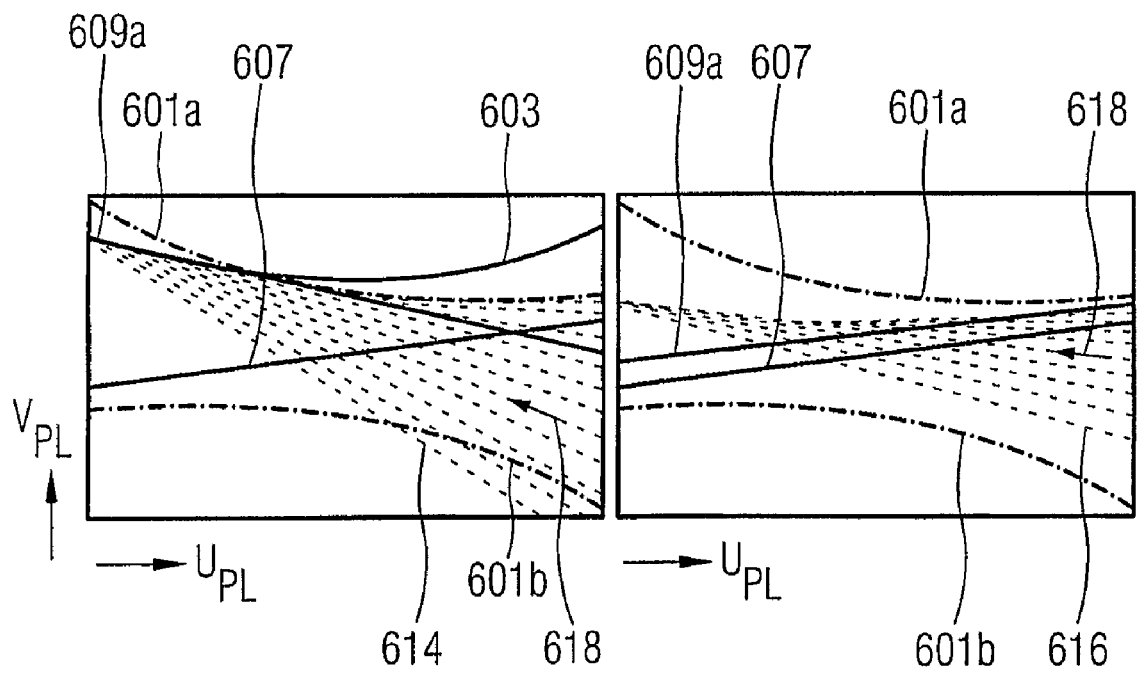

A second set of filter lines 614, 616 is shown in FIGS. 26 and 27 for two different focal spot positions on the portion of the helical trajectory wherein $z_0$ is negative. The helical detected values, which have been projected onto the virtual planar detector, are filtered along the filter lines 614, 616 from right to left, i.e. along the direction indicated by the arrows 618.

Above, the filter lines and the ignored helical detected data, i.e. the helical detected data, which are not filtered and which will further below not be backprojected, are described for helical detected data whose corresponding focal spot position is located on a side of the circular position which corresponds to the situations illustrated in FIGS. 20, 21, 23, i.e. for $z_0<0$. The above description of the filter lines can be analogously applied to situations, in which the focal spot is located on the opposite site of the circular position, i.e. for $z_0>0$, wherein the terms "upper projection 601a of the portion 503 of the helical trajectory" or the like has to be substituted by "lower projection 601b of the portion 503 of the helical trajectory". Furthermore, the terms "upper", above" etc. have to be substituted by "lower", "below" etc. and vice versa.

In particular, a first set of filter lines for helical detected data for $z_0>0$ is determined as follows. For a helical detected data value whose projection on the planar detector 605 is located above the asymptote 607, the corresponding filter line is parallel to the asymptote 607, i.e. parallel to the derivation $\dot{y}_\partial(s)$ of the portion 503 of the helical trajectory. If the projection of the helical detected data value is located below the asymptote 607, the corresponding filter line is either tangential to the projection 603 of the circular trajectory 501 or tangential to the lower projection 601b of the portion 503 of the helical trajectory, wherein the point of tangency is located on the left-hand side of the location of the projection of the corresponding helical detected value on the planar detector 605. The decision, whether the filter lines are tangential to the projection 603 of the circular trajectory 501 or tangential to the lower projection 601b of the portion 503 of the helical trajectory depends on the gradient of the corresponding tangents. If the gradient of the corresponding tangent of the projection 603 of the circular trajectory 501 is smaller than the tangent of the lower projection 601b of the portion 503 of the helical projection, the filter line is tangential to the projection 603 of the circular trajectory 501. If the gradient of the corresponding tangent of the of the projection 603 circular trajectory 501 is larger than the tangent of the lower projection 601b of the portion 503 of the helical projection, the filter line is tangential to the lower projection 601b of the portion 503 of the helical trajectory. The direction of filtering goes from left to right.

A second set of filter lines for $z_0>0$ is determined as follows. For a helical detected data value which has been projected onto the planar detector 605 the corresponding filter line is either tangential to the projection 603 of the circular trajectory 501 or tangential to the lower projection 601b of the portion 503 of the helical trajectory, wherein the point of tangency is located on the right-hand side of the location of the projection of the corresponding helical detected value on the planar detector 605. The decision, whether the filter lines are tangential to the projection 603 of the circular trajectory 501 or tangential to the lower projection 601b of the portion 503 of the helical trajectory depends on the gradient of the corresponding tangents. If the gradient of the corresponding tangent of the projection 603 of the circular trajectory 501 is smaller than the tangent of the lower projection 601b of the portion 503 of the helical projection, the filter line is tangential to the lower projection 601b of the portion 503 of the helical trajectory. If the gradient of the corresponding tangent of the projection 603 of the circular trajectory 501 is larger than the tangent of the lower projection 601b of the portion 503 of the helical projection, the filter line is tangential to the projection 603 of the circular trajectory 501. The direction of filtering goes from right to left.

After determination of the filter lines and the corresponding directions along the filter lines the detected data are filtered according to equation (26) using a $1/\sin\gamma$ filter.

A detected data value is parameterized by a combination of s and b, wherein for each circular detected data value one filter line is determined and wherein for each helical detected data value two filter lines are determined. If for a combination of s and b and a corresponding filter line a filtered detected data value P(s, b) is determined, the angle $\gamma$ is the angle between the vector b and the vector pointing from the focal spot position to the different detected data values, which have been projected onto the planar detector, on the corresponding filter line. Thus, the angle $\gamma$ samples the different detected data values along the corresponding filter line. A more detailed description of this $1/\sin\gamma$ filter is given in "A quasiexact reconstruction algorithm for helical CT using a 3-Pi acquisition", C. Bontus et. al., Med. Phys. 30(9) pp. 2493-2502 (2003).

A filter line, which has been determined for a helical detected value, which has been projected onto the planar detector, runs, of course, through this projected helical detected value, which can be parameterized by a combination of s and b.

In step 406 the filtered detected data are weighted according to equation (26) with the weights $\mu_q$. The filtered helical detected data which have been filtered along filter lines of the first set of filter lines are weighted with one half. Also, the filtered helical detected data which have been filtered along filter lines of the second set of filter lines are weighted with one half. The filtered circular detected data are weighted with one.

In step 407, according to equation (16), the weighted filtered helical data which have been filtered along filter lines of the first set of filter lines, the weighted filtered helical data which have been filtered along the filter lines of the second set of filter lines and the weighted filtered circular detected data are backprojected, wherein each data value is divided by the distance between the corresponding position y of the focal spot and the location x of the object of interest, i.e. the position of the voxel of the image, which has to be reconstructed.

If all locations x of the object of interest have been reconstructed by backprojection, the image has been reconstructed and the reconstruction terminates in step 408.

Although, the filter lines and directions along these filter lines are defined using projections on a virtual planar detector, the invention can also be carried out, without using this planar detector. This virtual planar detector is used only to illustrate the filter lines and the direction along these filter lines for the detected data values.

Figure 17:
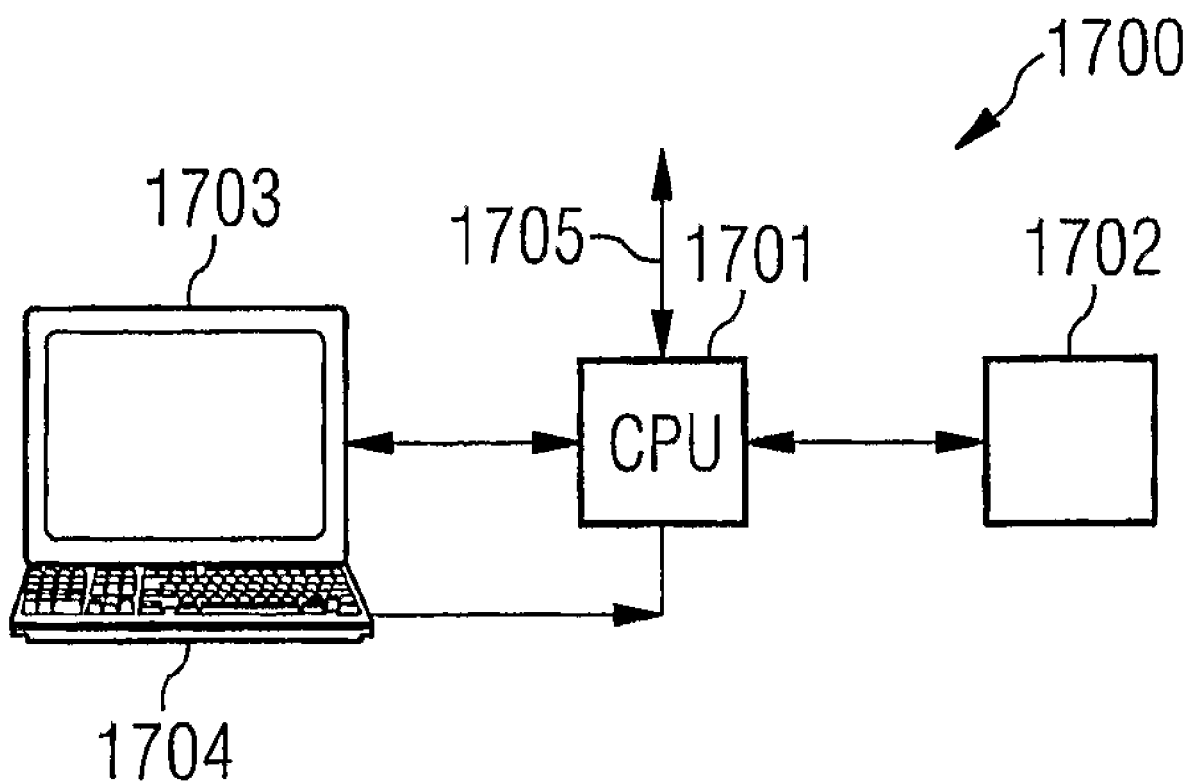
FIG. 17 shows an exemplary embodiment of a data processing device to be implemented in the computer tomography apparatus of the invention.

FIG. 17 depicts an exemplary embodiment of a data processing device 1700 according to the present invention for executing an exemplary embodiment of a method in accordance with the present invention. The data processing device 1700 depicted in FIG. 17 comprises a central processing unit (CPU) or image processor 1701 connected to a memory 1702 for storing an image depicting an object of interest, such as a patient. The data processor 1701 may be connected to a plurality of input/output network or diagnosis devices, such as a CT device. The data processor 1701 may furthermore be connected to a display device 1703, for example a computer monitor, for displaying information or an image computed or adapted in the data processor 1701. An operator or user may interact with the data processor 1701 via a keyboard 1704 and/or other output devices, which are not depicted in FIG. 17. Furthermore, via the bus system 1705, it is also possible to connect the image processing and control processor 1701 to, for example a motion monitor, which monitors a motion of the object of interest. In case, for example, a lung of a patient is imaged, the motion sensor may be an exhalation sensor. In case the heart is imaged, the motion sensor may be an electrocardiogram (ECG).

Exemplary technical fields, in which the present invention may be applied advantageously, include baggage inspection, medical applications, material testing, and material science. An improved image quality and less artefacts in combination with a low effort may be achieved. Also, the invention can be applied in the field of heart scanning to detect heart diseases.

It should be noted that the term "comprising" does not exclude other elements or steps and the "a" or "an" does not exclude a plurality. Also elements described in association with different embodiments may be combined.

It should also be noted that reference signs in the claims should not be construed as limiting the scope of the claims.

The invention claimed is:

1. A computer tomography apparatus for examination of an object of interest, the computer tomography apparatus comprising an electromagnetic radiation source adapted to emit electromagnetic radiation to an object of interest;

a detecting device adapted to detect electromagnetic radiation generated by the electromagnetic radiation source and passed through the object of interest;

a motion generation device adapted to move the electromagnetic radiation source and the detecting device with respect to the object of interest along a first trajectory and along at least one second trajectory which differs from the first trajectory, wherein the at least one second trajectory is selected in such a manner that electromagnetic radiation detected during performing the at least one second trajectory provides data which complete mathematically incomplete data detected during performing the first trajectory to thereby allow a reconstruction of structural information concerning the object of interest; and a determination unit adapted to determine the structural information based on signals received by the detecting device during performing the first trajectory and during performing the at least one second trajectory, wherein the structural information is determined without using helical data values whose projected helical data values on a planar detector:

(i) are disposed below or above a projection of a circular trajectory, (ii) are disposed below a lower projection or above a higher projection of adjacent windings of a portion of a helical trajectory or (iii) are disposed below a lower line or above a higher line to tangency and which comprise a coordinate on the planar detector which is disposed between two points of tangency of the lower or upper line of tangency.

2. The computer tomography apparatus according to claim 1, wherein the motion generation device is adapted in such a manner that the first trajectory precedes the at least one second trajectory.

3. The computer tomography apparatus according to claim 1, wherein the motion generation device is adapted in such a manner that the first trajectory succeeds the at least one second trajectory.

4. The computer tomography apparatus according to claim 1, wherein the motion generation device is adapted in such a manner that the at least one second trajectory comprises a first portion preceding the first trajectory and a second portion succeeding the first trajectory.

5. The computer tomography apparatus according to claim 1, wherein the motion generation device is adapted in such a manner that the first trajectory is at least a portion of a circular trajectory or is at least a portion of a helical trajectory.

6. The computer tomography apparatus according to claim 1, wherein the motion generation device is adapted in such a manner that the at least one second trajectory is a linear trajectory or is at least a portion of a circular trajectory or is at least a portion of a helical trajectory.

7. The computer tomography apparatus according to claim 1, wherein the motion generation device is adapted in such a manner that the first trajectory and the at least one second trajectory are realized in a continuous manner.

8. The computer tomography apparatus according to claim 1, wherein the motion generation device is adapted in such a manner that the electromagnetic radiation source and the detecting device are rotated during performing the first trajectory and are rotated during performing the at least one second trajectory; the object of interest is linearly moved during performing the at least one second trajectory and is fixed during performing the first trajectory.

9. The computer tomography apparatus according to claim 8, wherein the motion generation device is adapted in such a manner that the at least one second trajectory comprises a first portion preceding the first trajectory and a second portion succeeding the first trajectory.

10. The computer tomography apparatus according to claim 1, wherein the motion generation device is adapted in such a manner that the electromagnetic radiation source and the detecting device are rotated during performing the first trajectory and are fixed during performing the at least one second trajectory; the object of interest is linearly moved during performing the at least one second trajectory and is fixed during performing the first trajectory.

11. The computer tomography apparatus according to claim 10, wherein the motion generation device is adapted in such a manner that the at least one second trajectory comprises a first portion preceding the first trajectory and a second portion succeeding the first trajectory.

12. The computer tomography apparatus according to claim 10, wherein the motion generation device is adapted in such a manner that the at least one second trajectory is performed during a pilot-scan.

13. The computer tomography apparatus according to claim 1, wherein the determination unit is adapted to determine structural information concerning the object of interest based on a filtered back-projection analysis.

14. The computer tomography apparatus according to claim 1, wherein the analysis comprises differentiating the detected data, filtering the detected data, and back-projecting the detected data.

15. The computer tomography apparatus according to claim 14, wherein back-projecting the detected data includes rebinning the detected data or rebinning the filtered data.

16. The computer tomography apparatus according to claim 14, wherein back-projecting the detected data includes rebinning the detected data into a parallel geometry.

17. The computer tomography apparatus according to claim 14, wherein filtering the detected data includes filtering the detected data along inclined filter lines.

18. The computer tomography apparatus according to claim 1, wherein the motion generation device comprises a rotatable gantry on which the electromagnetic radiation source and the detecting device are mounted.

19. The computer tomography apparatus according to claim 1, wherein the motion generation device comprises a linearly movable mounting device adapted to receive the object of interest.

20. The computer tomography apparatus according to claim 1, wherein the detecting device is realized as a single-slice detecting device.

21. The computer tomography apparatus according to claim 1, wherein the detecting device is realized as a multi-slice detecting device.

22. The computer tomography apparatus according to claim 1, configured as one of the group consisting of a baggage inspection apparatus, a medical application apparatus, a material testing apparatus and a material science analysis apparatus.

23. The computer tomography apparatus according to claim 1 wherein the determination unit is adapted to filter the detected data using a $1/\sin \gamma$ filter.

24. The computer tomography apparatus according to claim 1 wherein
the motion generation device is adapted in such a manner that the first trajectory is a circular trajectory, wherein the electromagnetic radiation source and detecting device perform a rotational movement with respect to the object of interest about a rotational axis,
the detection device is adapted to detect circular detected data during performing the circular trajectory and
the determination unit is adapted to filter the circular detected data along filter lines which are parallel to each other.

25. The computer tomography apparatus according to claim 1 wherein
the motion generation device is adapted in such a manner that the first trajectory is a circular trajectory and that the at least one second trajectory is a portion of a helical trajectory, wherein the electromagnetic radiation source and detecting device perform a rotational movement with respect to the object of interest about a rotational axis,
the detection device is adapted to detect circular detected data during performing the circular trajectory and to detect helical detected data during performing the portion of the helical trajectory and
the determination unit is adapted to filter the detected data along filter lines, wherein at least a part of the filter lines of the helical detected data are parallel to a tangent of the circular trajectory or to a tangent of the portion of the helical trajectory.

26. The computer tomography apparatus according to claim 25 wherein the determination unit is adapted to filter detected helical data according to steps, which are definable using a virtual planar detector containing the rotational axis, on which the circular trajectory and the portion of the helical trajectory have been projected and on which one asymptote, which has a positive gradient, to the projections of two adjacent windings of the portion of the helical trajectory on the planar detector is defined, these steps are:

(i) determining a first set of filtered values:

if the projection of the circular trajectory is located in the upper part of the planar detector, by filtering of helical detected data values, whose projections on the planar detector are disposed below the asymptote, along filter lines, which are parallel to the asymptote, and filtering of helical detected data values, whose projections on the planar detector are disposed above the asymptote, along filter lines, which are either tangential to the projection of the circular trajectory or tangential to an upper projection of the portion of the helical trajectory, wherein the point of tangency is located on the left hand side of the projection onto the planar detector of the respective helical detected data value, if the projection of the circular trajectory is located in the lower part of the planar detector, by filtering of helical detected data values, whose projections on the planar detector are disposed above the asymptote, along filter lines, which are parallel to the asymptote, and filtering of helical detected data values, whose projections on the planar detector are disposed below the asymptote, along filter lines, which are either tangential to the projection of the circular trajectory or tangential to the lower projection of the portion of the helical trajectory, wherein the point of tangency is located on the right hand side of the projection onto the planar detector of the respective helical detected data value, (ii) determining a second set of filtered values:

if the projection of the circular trajectory is located in the upper part of the planar detector, by filtering of helical detected data values along filter lines, which are either tangential to the projection of the circular trajectory or tangential to the upper projection of the portion of the helical trajectory, wherein the point of tangency is located on the left hand side of the projection onto the planar detector of the respective helical detected data value, if the projection of the circular trajectory is located in the lower part of the planar detector, by filtering of helical detected data values along filter lines, which are either tangential to the projection of the circular trajectory or tangential to the lower projection of the portion of the helical trajectory, wherein the point of tangency is located on the right hand side of the projection onto the planar detector of the respective helical detected data value.

27. The computer tomography apparatus according to claim 26 wherein, when the first set of filter lines is determined and if the projection of the circular trajectory is located in the upper part of the planar detector, the determination unit is adapted to filter helical detected data values, whose projections on the planar detector are disposed above the asymptote, along filter lines, which are tangential to the projection of the circular trajectory, if the tangent of the projection of the circular trajectory has a smaller gradient than the tangent of the upper projection of the portion of the helical trajectory, and which are tangential to the upper projection of the portion of the helical trajectory, if the tangent of the projection of the circular trajectory has a larger gradient than the tangent to the upper projection of the portion of the helical trajectory, and when the second set of filter lines is determined and if the projection of the circular trajectory is located in the upper part of the planar detector, the determination unit is adapted to filter helical detected data values, along filter lines, which are tangential to the projection of the circular trajectory, if the tangent of the projection of the circular trajectory has a larger gradient than the tangent of the upper projection of the portion of the helical trajectory, and which are tangential to the upper projection of the portion of the helical trajectory, if the tangent of the projection of the circular trajectory has a smaller gradient than the tangent of the projection of the portion of the helical trajectory, when the first set of filter lines is determined and if the projection of the circular trajectory is located in the lower part of the planar detector, the determination unit is adapted to filter helical detected data values, whose projections on the planar detector are disposed below the asymptote, along filter lines, which are tangential to the projection of the circular trajectory, if the tangent of the projection of the circular trajectory has a smaller gradient than the tangent of the lower projection of the portion of the helical trajectory, and which are tangential to the lower projection of the portion of the helical trajectory, if the tangent of the projection of the circular trajectory has a larger gradient than the tangent of the lower projection of the portion of the helical trajectory, and when the second set of filter lines is determined and if the projection of the circular trajectory is located in the lower part of the planar detector, the determination unit is adapted to filter helical detected data values, along filter lines, which are tangential to the projection of the circular trajectory, if the tangent of the projection of the circular trajectory has a larger gradient than the tangent of the lower projection of the portion of the helical trajectory, and which are tangential to the lower projection of the portion of the helical trajectory, if the tangent of the projection of the circular trajectory has a smaller gradient than the tangent of the lower projection of the portion of the helical trajectory.

28. The computer tomography apparatus according to claim 27, wherein the determination unit is adapted to perform the filtering along the first set of filter lines from left to right and to perform the filtering along the second set of filter lines from right to left.

29. The computer tomography apparatus according to claim 28, wherein the determination unit is adapted to weight and back project the helical detected data filtered with the first data set of filter lines, the helical detected data filtered with the second data set of filter lines and the filtered circular detected data.

30. The computer tomography apparatus according to claim 29 wherein the determination unit is adapted to weight filtered circular detected data with one, to weight the filtered helical detected data filtered with the first set of filter lines with one half and to weight the filtered helical detected data filtered with the second set of filter lines with one half.

31. The computer tomography apparatus according to claim 1 wherein the motion generation device is adapted in such a manner that the first trajectory is a circular trajectory and that the at least one second trajectory is a portion of a helical trajectory, wherein the electromagnetic radiation source and detecting device perform a rational movement with respect to the object of interest about a rotational axis, the detection device is adapted to detect circular detected data during performing the circular trajectory and helical detected data during performing the portion of the helical trajectory and the determination unit is adapted to determine structural information concerning the object of interest according to a step, which is definable using a virtual planar detector containing the rotational axis, on which the circular trajectory and the portion of the helical trajectory have been projected, on which one asymptote, which has a positive gradient, to the projections of two adjacent windings of the portion of the helical trajectory on the planar detector is defined and on which an upper line of tangency, which is tangential to the projection of the circular trajectory and to the upper projection of the adjacent windings of the portion of the helical trajectory, and an lower line of tangency, which is tangential to the projection of the circular trajectory and to the lower projection of the adjacent windings of the portion of the helical trajectory, are defined, this step is, if the projection of the circular trajectory is located in the upper part of the planar detector,
determine structural information concerning the object of interest without using helical data values whose projected helical data values on the planar detector
(i) are disposed above the projection of the circular trajectory,
(ii) are disposed above the upper projection of the adjacent windings of the portion of the helical trajectory or
(iii) are disposed above the upper line of tangency and which comprise an $u_{PL}$ coordinate on the planar detector which is disposed between two points of tangency of the upper line of tangency, and this step is, if the projection of the circular trajectory is located in the lower part of the planar detector,
determine structural information concerning the object of interest without using helical data values whose projected helical data values on the planar detector
(i) are disposed below the projection of the circular trajectory,
(ii) are disposed below the lower projection of the adjacent windings of the portion of the helical trajectory or
(iii) are disposed below the lower line to tangency and which comprise an $u_{PL}$ coordinate on the planar detector which is disposed between two points of tangency of the lower line of tangency.

32. A method of examining an object of interest, the method comprising the steps of
emitting electromagnetic radiation to an object of interest by an electromagnetic radiation source;
detecting, by a detecting device, electromagnetic radiation generated by the electromagnetic radiation source and passed through the object of interest;
moving the electromagnetic radiation source and the detecting device with respect to the object of interest along a first trajectory and along a second trajectory which differs from the first trajectory, wherein the second trajectory is selected in such a manner that electromagnetic radiation detected during performing the second trajectory provides data which complete mathematically incomplete data detected during performing the first trajectory to thereby allow a reconstruction of structural information concerning the object of interest;

filtering, if a projection of a circular trajectory is located in an upper part of a planar detector, helical detected data values with projections on the planar detector that are disposed below an asymptote along filter lines which are parallel to the asymptote and helical detected data values with projections on the planar detector that are disposed above the asymptote, along filter lines, which are either tangential to the projection of the circular trajectory or tangential to an upper projection of the portion of the helical trajectory, wherein the point of tangency is located on the left hand side of the projection onto the planar detector of the respective helical detected data value, and filtering, if the projection of the circular trajectory is located in the lower part of the planar detector, helical detected data values with projections on the planar detector that are disposed above the asymptote, along filter lines, which are parallel to the asymptote, and helical detected data values with projections on the planar detector that are disposed below the asymptote, along filter lines, which are either tangential to the projection of the circular trajectory or tangential to the lower projection of the portion of the helical trajectory, wherein the point of tangency is located on the right hand side of the projection onto the planar detector of the respective helical detected data value.

33. The method of claim 32, further comprising:
filtering, if the projection of the circular trajectory is located in the upper part of the planar detector, helical detected data values along filter lines, which are either tangential to the projection of the circular trajectory or tangential to the upper projection of the portion of the helical trajectory, wherein the point of tangency is located on the left hand side of the projection onto the planar detector of the respective helical detected data value, and filtering, if the projection of the circular trajectory is located in the lower part of the planar detector, helical detected data values along filter lines, which are either tangential to the projection of the circular trajectory or tangential to the lower projection of the portion of the helical trajectory, wherein the point of tangency is located on the right hand side of the projection onto the planar detector of the respective helical detected data value.

34. A non-transient computer-readable medium, in which a computer program of examining an object of interest is stored which, when being executed by a processor, is adapted to carry out the steps of
emitting electromagnetic radiation to an object of interest by an electromagnetic radiation source;
detecting, by a detecting device, electromagnetic radiation generated by the electromagnetic radiation source and passed through the object of interest;
moving the electromagnetic radiation source and the detecting device with respect to the object of interest along a first trajectory and along a second trajectory which differs from the first trajectory, wherein the second trajectory is selected in such a manner that electromagnetic radiation detected during performing the second trajectory provides data which complete mathematically incomplete data detected during performing the first trajectory to thereby allow a reconstruction of structural information concerning the object of interest; and determining structural information concerning the object of interest based on an analysis of detecting signals received by the detecting device during performing the first trajectory and during performing the at least one second trajectory including determining the structural information without using helical data values whose projected helical data values on a planar detector, wherein the first trajectory is a circular trajectory and that the at least one second trajectory is a portion of a helical trajectory.

* * * * *